(12) United States Patent
Ohga

(10) Patent No.: US 10,593,026 B2
(45) Date of Patent: Mar. 17, 2020

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventor: Manabu Ohga, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 107 days.

(21) Appl. No.: 15/896,960

(22) Filed: Feb. 14, 2018

(65) Prior Publication Data

US 2018/0247393 A1    Aug. 30, 2018

(30) Foreign Application Priority Data

Feb. 27, 2017    (JP) .................................. 2017-034504

(51) Int. Cl.
*G06T 5/00*    (2006.01)
*H04N 5/232*   (2006.01)
(Continued)

(52) U.S. Cl.
CPC ............. *G06T 5/006* (2013.01); *G01N 21/55* (2013.01); *G06T 3/0018* (2013.01);
(Continued)

(58) Field of Classification Search
CPC .... G01S 5/0252; G05D 1/0251; G05D 1/028; G05D 2201/0217; G05D 1/0274;
(Continued)

(56) References Cited

U.S. PATENT DOCUMENTS 5,710,876 A * 1/1998 Peercy ................. G06T 15/506
                                                345/426
5,923,334 A * 7/1999 Luken .................. G06T 15/205
                                                345/423
(Continued)

FOREIGN PATENT DOCUMENTS

JP    2003-203220 A    7/2003
JP    2005-259009 A    9/2005

OTHER PUBLICATIONS

Paul E. Debevec et al. ; "Recovering High Dynamic Range Radiance Maps from Photographs;" Computer Science Division, University of California at Berkeley; In Proc. ACM SIGGRAPH 97, pp. 369-378.

(Continued)

*Primary Examiner* — Aklilu K Woldemariam
(74) *Attorney, Agent, or Firm* — Canon U.S.A., Inc. IP Division

(57) ABSTRACT

An apparatus includes a first acquisition unit configured to, with a viewpoint set to a position of an object, acquire a plurality of environment maps for each position of light sources, the environment maps being obtained by imaging a surrounding environment from the viewpoint, a second acquisition unit configured to acquire a plurality of captured images for each position of the light sources, the captured images being obtained by imaging from a plurality of directions the object irradiated with light by the light sources, and a determination unit configured to determine reflection characteristics of the object based on the environment maps and the plurality of captured images.

20 Claims, 21 Drawing Sheets

(51) Int. Cl.
*H04N 5/262* (2006.01)
*G06T 3/00* (2006.01)
*G06T 15/60* (2006.01)
*G06T 15/20* (2011.01)
*H04N 7/18* (2006.01)
*G06T 15/04* (2011.01)
*G06T 15/50* (2011.01)
*G01N 21/55* (2014.01)

(52) U.S. Cl.
CPC ............ *G06T 3/0037* (2013.01); *G06T 15/04* (2013.01); *G06T 15/205* (2013.01); *G06T 15/506* (2013.01); *G06T 15/60* (2013.01); *H04N 5/23238* (2013.01); *H04N 5/23293* (2013.01); *H04N 5/2628* (2013.01); *H04N 7/185* (2013.01); *G06T 2215/12* (2013.01)

(58) Field of Classification Search
CPC .. G05D 1/0246; G05D 1/0255; G05D 1/0272; G06N 3/008; G01N 21/55; G06T 15/04; G06T 15/205; G06T 15/506; G06T 15/60; G06T 2215/12; G06T 3/0018; G06T 3/0037; G06T 5/006; G06T 11/001; G06T 11/40; G06T 2200/24; G06T 2215/16; H04N 5/23238; H04N 5/23293; H04N 5/2628; H04N 7/185; H04N 7/181; H04N 13/243; H04N 13/271; A47L 9/2805; A47L 9/281; A47L 9/2852; A47L 9/2894; A47L 2201/04; G06F 3/0354; G06F 3/0484; B25J 9/1664; G05B 2219/36513; G05B 2219/40423; G02B 2027/0138; G02B 2027/014

USPC ......... 382/293; 345/419, 423, 426; 700/245, 700/263
See application file for complete search history.

(56) References Cited

U.S. PATENT DOCUMENTS

| | | | |
|---|---|---|---|
| 9,001,226 B1* | 4/2015 | Ng | H04N 5/23203 348/211.11 |
| 9,460,553 B2* | 10/2016 | Tabellion | G06T 17/005 |
| 2002/0063225 A1* | 5/2002 | Payton | G01D 21/00 250/559.22 |
| 2006/0202985 A1* | 9/2006 | Kobayashi | G06T 15/04 345/419 |
| 2007/0061043 A1* | 3/2007 | Ermakov | A47L 5/225 700/263 |
| 2008/0086236 A1* | 4/2008 | Saito | G01S 5/0252 700/245 |
| 2011/0010033 A1* | 1/2011 | Asahara | G05D 1/024 701/26 |
| 2013/0194254 A1* | 8/2013 | Miyoshi | G06T 15/005 345/419 |

OTHER PUBLICATIONS

Min H. Kim et al.; "Characterization for High Dynamic Range Imaging;" Eurographics, vol. 27 (2008), No. 2, pp. 691-697.

* cited by examiner

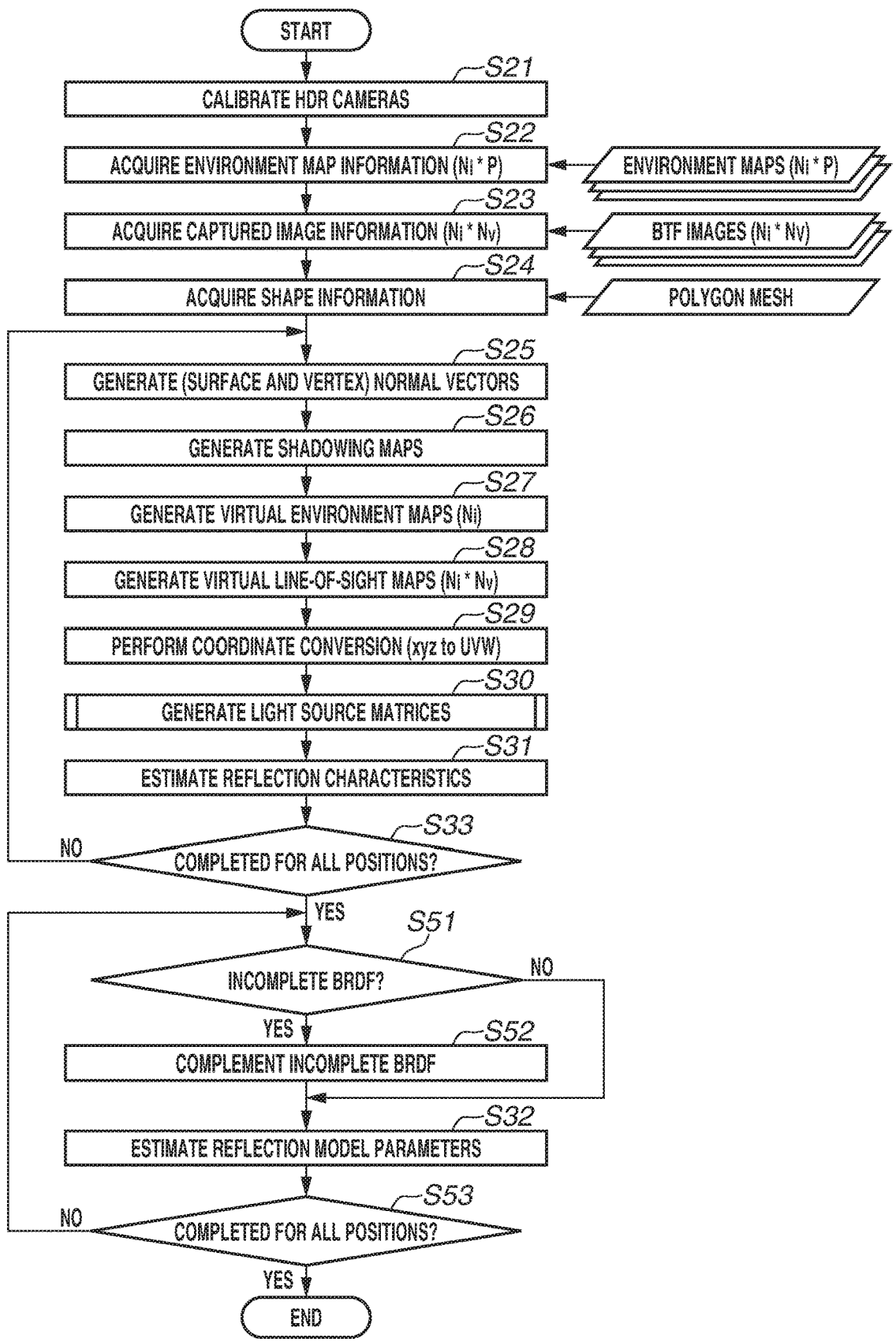

IMAGE PROCESSING APPARATUS, IMAGE PROCESSING METHOD, AND STORAGE MEDIUM

BACKGROUND OF THE INVENTION

Field of the Invention

The aspect of the embodiments relates to an image processing technique of estimating reflection characteristics of a real object.

Description of the Related Art

A conventional method of estimating surface attributes such as reflection characteristics of a real object is known to measure the Bidirectional Reflectance Distribution Function (BRDF) of the real object by using a goniophotometer.

Japanese Patent Application Laid-Open No. 2003-203220 discusses a technique of estimating the BRDF of a real object by performing a deconvolution operation, based on the luminance distribution of illumination light, on luminance changes in captured images of the real object irradiated with the illumination light from light sources having a two-dimensionally spread luminance distribution.

Japanese Patent Application Laid-Open No. 2005-259009 discusses a technique of estimating, by using Wiener estimation, the BRDF of a real object by generating an estimation matrix for estimating the BRDF of the real object based on pixel value vectors in consideration of the illumination light distribution at the time of measurement.

However, the techniques discussed in Japanese Patent Application Laid-Open No. 2003-203220 and Japanese Patent Application Laid-Open No. 2005-259009 have not taken external light other than illumination light and ambient light into consideration in the reflection characteristic estimation of a real object. More specifically, the technique discussed in Japanese Patent Application Laid-Open No. 2003-203220 represents the luminance distribution of illumination light by using a function of angular deviation from the light source center direction. The technique discussed in Japanese Patent Application Laid-Open No. 2005-259009 takes into consideration the illumination light distribution at the time of measurement by considering that light from a plurality of adjacent point light sources configuring a light source surface has different incident angles. Therefore, there has been a situation that the measurement accuracy of the BRDF degrades in an environment where measurement is affected by external light and reflected light from surrounding frames. More specifically, in measurement with the conventional technique, it has been necessary to provide restrictions on the measurement environment to eliminate the influence of external light and indirect light. Examples of restrictions include measurement in a darkroom and the use of black-painted frames for restricting reflected light.

In the conventional technique, there has been an assumption for simplicity that illumination light from light sources is parallelly radiated to all points on a real object. Therefore, if there are no actual light sources at an infinite point, an error has occurred in the BRDF measurement. Particularly in a case of a three-dimensional real object, the magnitude of an error increases as size of the real object increases relative to the distance to the light sources. Although a certain method repeats light irradiation and imaging while controlling the lighting direction or the viewing direction for each point on the three-dimensional real object so as to reduce error, the method has not been practical since an enormous amount of time is required.

SUMMARY OF THE INVENTION

According to an aspect of the embodiments, an apparatus includes a first acquisition unit configured to, with a viewpoint set to a position of an object, acquire a plurality of environment maps for each position of light sources, the environment maps being obtained by imaging a surrounding environment from the viewpoint, a second acquisition unit configured to acquire a plurality of captured images for each position of the light sources, the captured images being obtained by imaging from a plurality of directions the object irradiated with light by the light sources, and a determination unit configured to determine reflection characteristics of the object based on the environment maps and the plurality of captured images.

Further features of the disclosure will become apparent from the following description of exemplary embodiments with reference to the attached drawings.

BRIEF DESCRIPTION OF THE DRAWINGS

FIG. 21 is a flowchart illustrating estimation processing of reflection characteristics of a three-dimensional real object in consideration of shadowing.

DESCRIPTION OF THE EMBODIMENTS

Figure 1:
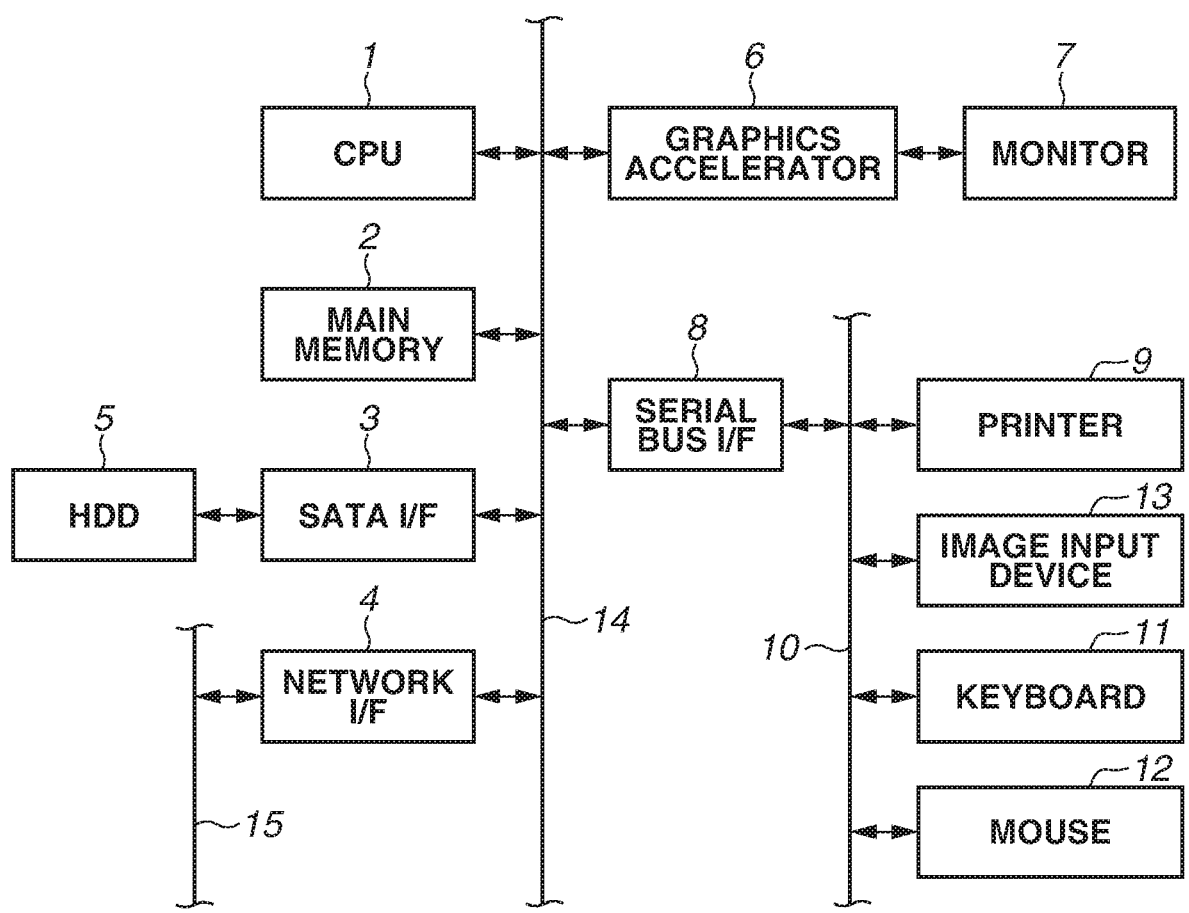
FIG. 1 is a block diagram illustrating an example of a configuration of an image processing apparatus.

Exemplary embodiments of the disclosure will be described in detail below with reference to the accompanying drawings. The following exemplary embodiments in this disclosure are to be considered as illustrative examples, and may be corrected, modified, and combined as required depending on the configuration of an apparatus for which the disclosure is used and other various conditions. The disclosure is not limited to the following exemplary embodiments. Not all of the combinations of the features described in the exemplary embodiments are indispensable to the solutions for the disclosure. In the following descriptions, identical configurations or identical pieces of processing are assigned the same reference numerals.

(Configuration of Image Processing Apparatus)

FIG. 1 is a block diagram illustrating an example of a configuration of an image processing apparatus according to the first exemplary embodiment.

The image processing apparatus includes a central processing unit (CPU) 1, a main memory 2, a Serial AT Attachment (SATA) interface (I/F) 3, a network I/F 4, a hard disk drive (HDD) 5, a graphics accelerator 6, a monitor 7, a serial bus I/F 8, a printer 9, and a serial bus 10. The image processing apparatus further includes a keyboard 11, a mouse 12, an image input device 13, and a system bus 14.

The main memory 2 includes a random access memory (RAM) and a read only memory (ROM). The CPU 1 executes an operating system (OS) and various programs stored in the ROM of the main memory 2 and the hard disk drive (HDD) 5, by using the RAM of the main memory 2 as a work memory. Then, the CPU 1 controls each configuration via the system bus 14 such as a Peripheral Component Interconnect (PCI) bus. The CPU 1 further executes various programs including image processing (described below).

The CPU 1 accesses the HDD 5 via the system bus 14 and the SATA I/F 3 and accesses a network 15 such as a local area network (LAN) via the network I/F 4.

The CPU 1 communicates with the serial bus I/F 8, a Universal Serial Bus (USB), and devices connected to the serial bus 10 of an Institute of Electrical and Electronics Engineers (IEEE) 1394 standard. The CPU 1 acquires image data and three-dimensional (3D) data subjected to image processing from the image input device 13 including a card reader and outputs image data and 3D data including control parameters (described below) to the printer 9, for example, to print an image and shape a 3D object, which is specified by the user. The CPU 1 may read image data and 3D data subjected to image processing from the HDD 5 or a server on the network 15.

The CPU 1 displays a user interface for processing (described below) and a processing result on the monitor 7 via the graphics accelerator 6, and inputs an instruction from the user via the keyboard 11 and the mouse 12 connected to the serial bus 10.

Although, in the present exemplary embodiment, each piece of the following image processing will be described below on the premise that functions are implemented as software programs, a part or all of functions included in the function block may be configured by hardware. When functions are implemented by hardware, for example, a dedicated circuit on a Field Programmable Gate Array (FPGA) by using a predetermined compiler based on a program for implementing each step is automatically generated. Similar to a FPGA, a Gate Array circuit may be formed to implement functions as hardware. Further, functions may be implemented by an Application Specific Integrated Circuit (ASIC).

(Configuration of Image Input Device)

Figure 2A:
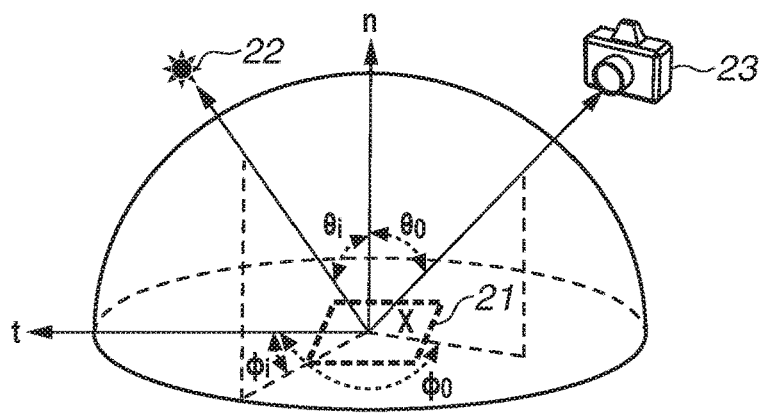
FIGS. 2A, 2B, and 2C are conceptual views illustrating examples of configurations of an image input device.
Figure 2B:
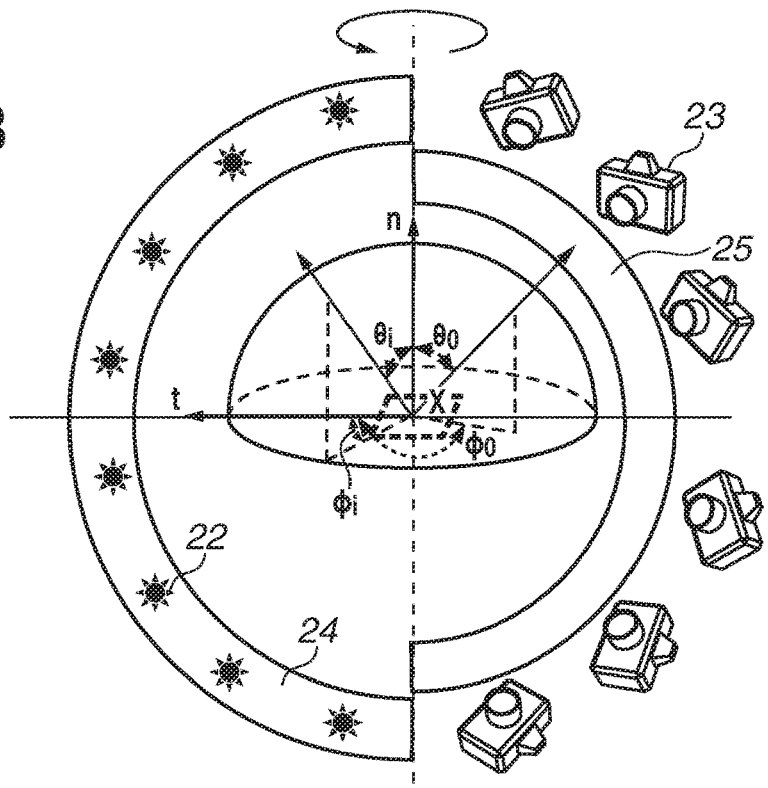
Figure 2C:
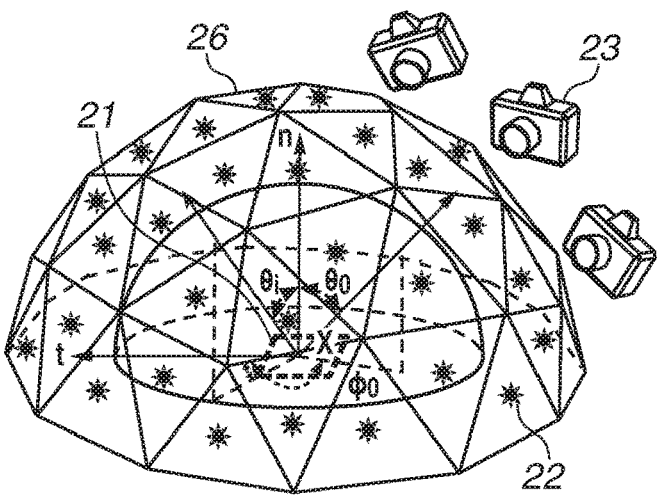

FIGS. 2A, 2B, and 2C are conceptual views illustrating examples of configurations of the image input device 13 according to the present exemplary embodiment.

As illustrated in FIG. 2A, the image input device 13 includes, for example, a light source 22 for irradiating a real object 21 with illumination light, and a digital camera 23 for imaging the real object 21 irradiated with illumination light by the light source 22.

The light source 22 can irradiate the real object from an arbitrary angle. The lighting direction is defined by $(\theta_i, \varphi_i)$. The digital camera 23 can image the real object 21 from an arbitrary angle. The viewing direction is defined by $(\theta_o, \varphi_o)$. In $(\theta, \varphi)$, $\theta$ denotes the polar angle with respect to a surface normal (n), and $\varphi$ denotes the azimuth angle with respect to a reference direction (t) with a point X on the real object 21 set as the origin. The light source 22 and the digital camera 23 do not need to be limited to one in number, i.e., a plurality of light sources or a plurality of digital cameras may be used at the same time.

FIG. 2B illustrates an example of a configuration of the image input device 13 in which a plurality of the light sources 22 having different lighting directions is arranged on a light source semicircular arc arm 24, and a plurality of the digital cameras 23 having different viewing directions is arranged on an imaging semicircular arc arm 25. Since the light source semicircular arc arm 24 and the imaging semicircular arc arm 25 can be independently rotated in azimuth angle directions around the point X on the real object 21, the real object 21 irradiated with illumination light from different directions can be simultaneously imaged from a plurality of directions. In addition, the real object 21 may be rotated by using a turntable together.

FIG. 2C illustrates an example of a configuration in which a plurality of the light sources 22 and a plurality of the digital cameras 23 are arranged on a geodesic dome 26. The shape of the geodesic dome 26 is not limited to a hemisphere and may be a sphere. In this configuration, since it is not necessary to rotate the light source semicircular arc arm 24 and the imaging semicircular arc arm 25 or rotate the real object 21 on the turntable, the imaging time can be further shortened.

(Operation Overview)

The following describes operations of the image processing apparatus according to the present exemplary embodiment.

The image processing apparatus first acquires information about captured images (captured image information) of the real object 21 and environment map information via the image input device 13, and supplies these pieces of information to the CPU 1. The image processing apparatus also estimates the reflection characteristics of the real object 21 through processing by the CPU 1.

(Acquiring Environment Map Information)

Figure 3A:
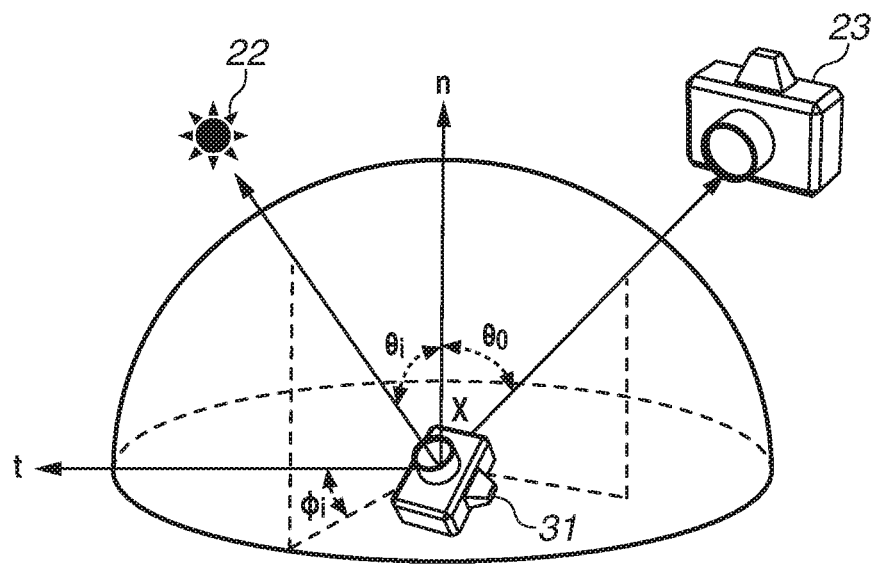
FIGS. 3A and 3B are conceptual views illustrating an example of processing for acquiring environment map information and captured image information.

FIG. 3A is a conceptual view illustrating an example of processing for acquiring the environment map information according to the present exemplary embodiment.

The image input device 13 is capable of imaging the real object 21 irradiated with light from the light source, from an arbitrary angle while changing the pattern of the light source (hereinafter referred to as a "light source pattern") including direct light for irradiating the real object 21 and indirect light.

To associate the light source pattern including direct light and indirect light with the captured image information for the real object 21 irradiated with the light source, the image input device 13 acquires the light source pattern including direct light and indirect light as the environment map information, and supplies the information to the CPU 1. The image input device 13 acquires the environment map information for each of a plurality of light source patterns. More specifically, the image input device 13 acquires a plurality of pieces of environment map information for a plurality of light source patterns.

For example, as illustrated in FIG. 3A, the environment map information can be acquired by using an omnidirectional camera 31. More specifically, the image input device 13 acquires a light source pattern by extensively imaging the surrounding environment from a viewpoint on the real object 21. Alternatively, the environment map information can also be acquired by using a camera with a fish-eye lens or a mirror ball instead of the omnidirectional camera 31. The environment map information is a spherical or hemispherical light source pattern, and a viewpoint of the environment map information coincides with the point X on the real object 21.

A High Dynamic Range (HDR) camera with a high dynamic range is used as the omnidirectional camera 31 and the digital camera 23.

(Environment Map Information and Captured Image Information)

Figure 3B:
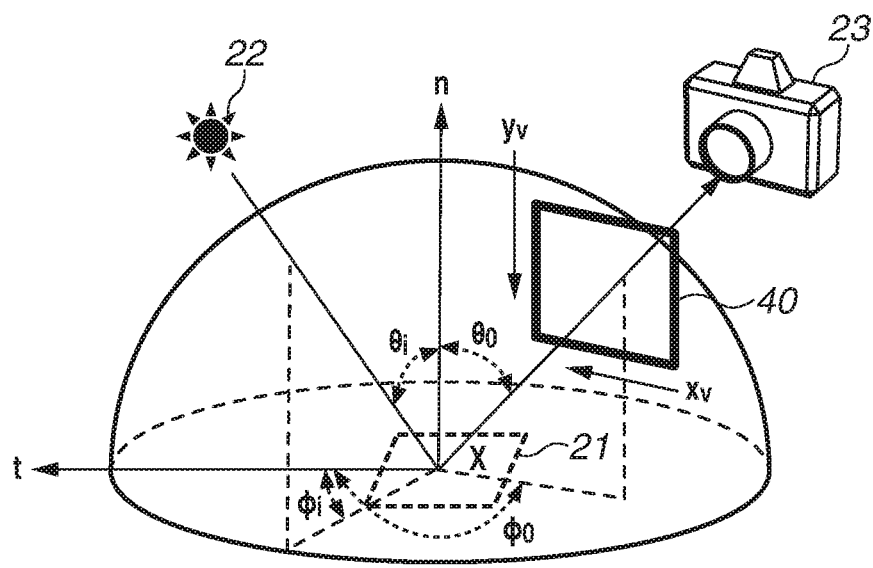

FIG. 3B is a conceptual view illustrating an example of processing for acquiring the captured image information according to the present exemplary embodiment. FIG. 3B illustrates a captured image 40 of the real object 21 irradiated with the light source pattern. Each time an illumination condition of the light source pattern including direct light by the light source 22 and indirect light changes, the image input device 13 acquires the captured image 40 of the real object 21 by using the digital camera 23.

More specifically, for each of a plurality of light source patterns, the image input device 13 acquires image information by imaging the real object 21 irradiated with the light source 22 from a plurality of viewing directions.

Figure 4A:
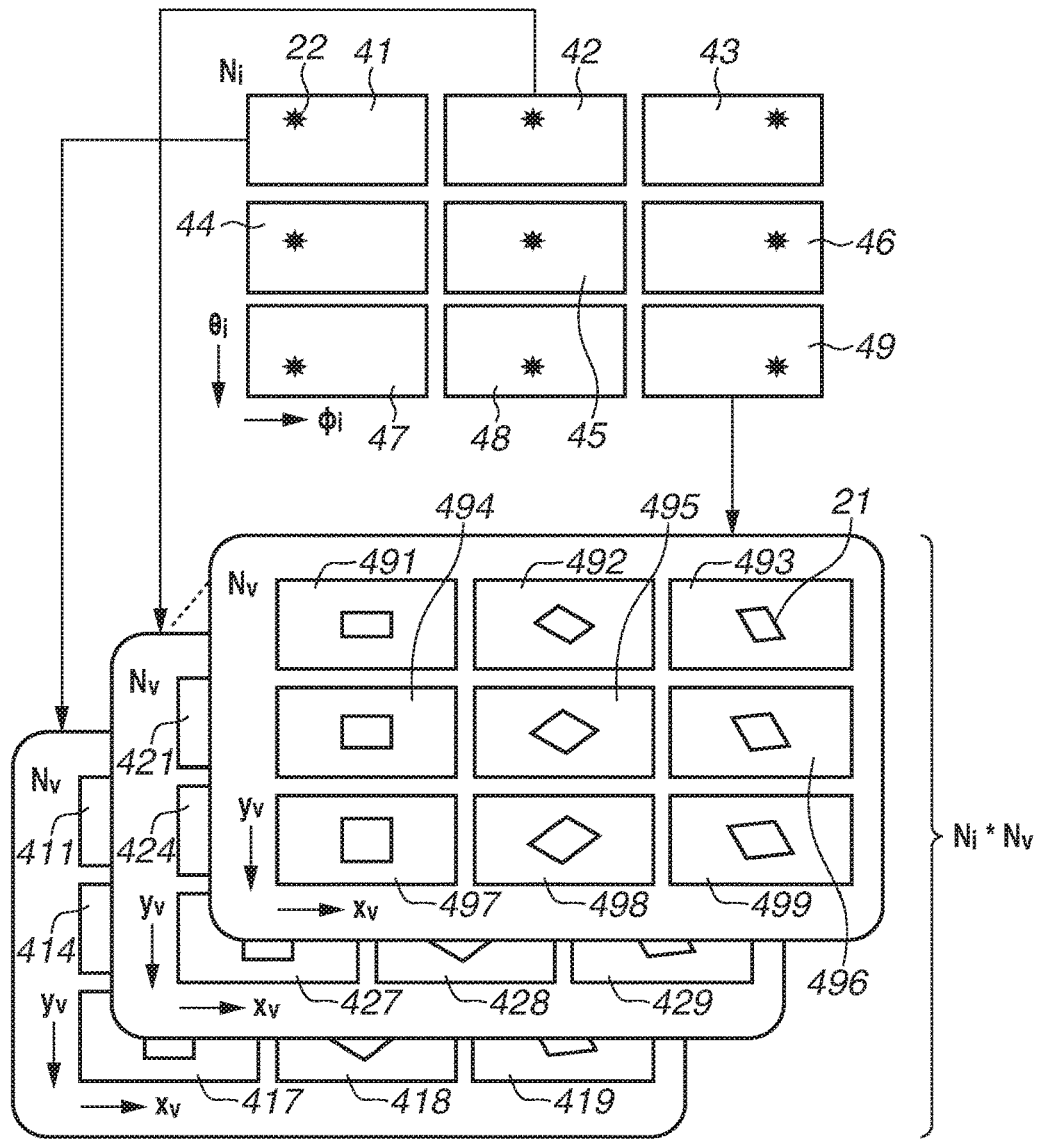
FIGS. 4A and 4B illustrates a relation between environment map information and captured image information and an example of segmentation solid angles.
Figure 4B:
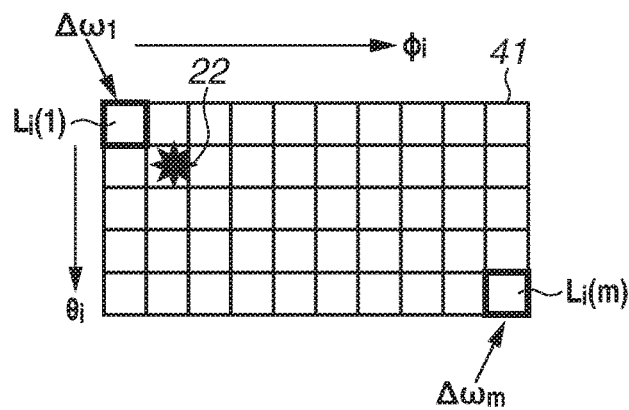

FIGS. 4A and 4B are conceptual views illustrating a relation between the environment map information (environment maps) and the captured image information, and an example of segmentation solid angles according to the present exemplary embodiment.

FIG. 4A illustrates a relationship between the environment map information (environment maps 41 to 49) acquired by using the omnidirectional camera 31 for light source patterns in 9 different lighting directions and images 411 to 499 of the real object 21 captured from 9 different viewing directions for each light source pattern. The number of lighting directions and the number of viewing directions do not need to be limited to 9. When $N_i$ denotes the number of light source patterns and $N_v$ denotes the number of viewing directions, the number of environment maps is $N_i$ and the total number of captured images is given by $N_i*N_v$. In this case, the environment maps are omnidirectional images and are represented, for example, in the equirectangular projection format with a vertical axis $\theta_i$ (polar angle) and a horizontal axis $\varphi_i$ (azimuth angle). The captured image information is represented by a horizontal axis $x_v$ [pixel] and a vertical axis $y_v$ [pixel]. If the optical axis of the digital camera 23 coincides with the point X on the real object 21, the center pixel of the captured image information is represented by $(\theta_o, \varphi_o)$.

(Estimating Reflection Characteristics of Real Object)

The CPU 1 of the image processing apparatus estimates the reflection characteristics of the real object based on the environment map information and the captured image information. Estimating the reflection characteristics is also referred to as determining the reflection characteristics.

Generally, the bidirectional reflectance distribution function BRDF is defined by the formula (1).

$$f_r(x, \omega_i, \omega_r) = \frac{dL_o(x, \omega_r)}{dE_i(x, \omega_i)} = \frac{dL_o(x, \omega_r)}{L_i(x, \omega_i)\cos(\theta_i)d\omega_i} \quad (1)$$

Here, $f_r$ denotes BRDF [1/sr], $L_o$ denotes the radiation luminance [W/sr/m²] in the viewing direction, Ei denotes the radiation illuminance [W/m²], $L_i$ denotes the radiation luminance [W/sr/m²] in the lighting direction, and $\theta_i$ denotes the angle (polar angle) formed between the lighting direction and the surface normal of the real object 21, x denotes the position coordinates of the point X, $\omega_i$ denotes the lighting direction (solid angle [sr]), and $\omega_r$ denotes the viewing direction (solid angle [sr]).

Solving the formula (1) for the radiation luminance $L_o$ in the viewing direction rearranges the formula (1) into the rendering formula (2).

$$L_o(x, \omega_r) = L_e(x, \omega_r) + \int_\Omega L_i(x, \omega_i) f_r(x, \omega_i, \omega_r) \cos(\theta_i) d\omega_i \quad (2)$$

Here, $L_e$ denotes the radiation luminance [W/sr/m²] of spontaneous light and $\Omega$ denotes the sphere $(4\pi)$ [sr] or hemisphere $(2\pi)$ [sr] of the entire solid angle.

For simplicity, taking the real object 21 that does not emit spontaneous light, as an example gives the formula (3).

$$L_o(x, \omega_r) = \int_\Omega L_i(x, \omega_i) f_r(x, \omega_i, \omega_r) \cos(\theta_i) d\omega_i \quad (3)$$

When a method of discretizing the formula (3) to segment the light source patterns of direct light radiated from all directions and indirect light into m segmentation solid angles $\Delta\omega_j$ (j=1 to m) is applied to each of the $N_i$ light source patterns, the simultaneous linear formula (4) is given for the viewing direction $k \in [1, N_v]$. In this case, there is a relation represented by the formula (5) between the omnidirectional solid angle $\Omega$ and the segmentation solid angles $\Delta\omega_j$ (j=1 to m).

$$L_o(x, k, 1) = \sum_{j=1}^{m} L_i(x, j, 1) f_r(x, j, k) \cos(\theta_j) \Delta\omega_j$$

$$L_o(x, k, 2) = \sum_{j=1}^{m} L_i(x, j, 2) f_r(x, j, k) \cos(\theta_j) \Delta\omega_j$$

$$\vdots$$

$$L_o(x, k, N_i) = \sum_{j=1}^{m} L_i(x, j, N_i) f_r(x, j, k) \cos(\theta_j) \Delta\omega_j \quad (4)$$

$$\sum_{j=1}^{m} \Delta\omega_j = \Omega \quad (5)$$

When the simultaneous linear formula (4) is to be expressed using a matrix, the formula (4) can be rearranged as the formula (6). When the formula (6) is solved for $f_r(x, 1, k)$ to $f_r(x, m, k)$ that are m BRDFs, the BRDFs for the m lighting directions (1 to m) and one viewing direction ($k \in [1, N_v]$) can be calculated by the formula (7).

$$\begin{pmatrix} L_o(x, k, 1) \\ L_o(x, k, 2) \\ \vdots \\ L_o(x, k, N_i) \end{pmatrix} = \begin{pmatrix} L_i(x, 1, 1) & L_i(x, 2, 1) & \ldots & L_i(x, m, 1) \\ L_i(x, 1, 2) & L_i(x, 2, 2) & \ldots & L_i(x, m, 2) \\ \vdots & \vdots & \vdots & \vdots \\ L_i(x, 1, N_i) & L_i(x, 2, N_i) & \ldots & L_i(x, m, N_i) \end{pmatrix}$$

$$\begin{pmatrix} f_r(x, 1, k)\cos(\theta_1)\Delta\omega_1 \\ f_r(x, 2, k)\cos(\theta_2)\Delta\omega_2 \\ \vdots \\ f_r(x, m, k)\cos(\theta_m)\Delta\omega_m \end{pmatrix}$$

$$= \begin{pmatrix} L_i(x, 1, 1)\cos(\theta_1)\Delta\omega_1 & L_i(x, 2, 1)\cos(\theta_2)\Delta\omega_2 & \ldots & L_i(x, m, 1)\cos(\theta_m)\Delta\omega_m \\ L_i(x, 1, 2)\cos(\theta_1)\Delta\omega_1 & L_i(x, 2, 2)\cos(\theta_2)\Delta\omega_2 & \ldots & L_i(x, m, 2)\cos(\theta_m)\Delta\omega_m \\ \vdots & \vdots & \vdots & \vdots \\ L_i(x, 1, N_i)\cos(\theta_1)\Delta\omega_1 & L_i(x, 2, N_i)\cos(\theta_2)\Delta\omega_2 & \ldots & L_i(x, m, N_i)\cos(\theta_m)\Delta\omega_m \end{pmatrix}$$

$$\begin{pmatrix} f_r(x, 1, k) \\ f_r(x, 2, k) \\ \vdots \\ f_r(x, m, k) \end{pmatrix}$$

$$= \begin{pmatrix} A \end{pmatrix} \begin{pmatrix} f_r(x, 1, k) \\ f_r(x, 2, k) \\ \vdots \\ f_r(x, m, k) \end{pmatrix} \quad (6)$$

$$\begin{pmatrix} f_r(x, 1, k) \\ f_r(x, 2, k) \\ \vdots \\ f_r(x, m, k) \end{pmatrix} = \begin{pmatrix} A^{-1} \end{pmatrix} \begin{pmatrix} L_o(x, k, 1) \\ L_o(x, k, 2) \\ \vdots \\ L_o(x, k, N_i) \end{pmatrix}$$

$$= \begin{pmatrix} L_i(x, 1, 1)\cos(\theta_1)\Delta\omega_1 & L_i(x, 2, 1)\cos(\theta_2)\Delta\omega_2 & \ldots & L_i(x, m, 1)\cos(\theta_m)\Delta\omega_m \\ L_i(x, 1, 2)\cos(\theta_1)\Delta\omega_1 & L_i(x, 2, 2)\cos(\theta_2)\Delta\omega_2 & \ldots & L_i(x, m, 2)\cos(\theta_m)\Delta\omega_m \\ \vdots & \vdots & \vdots & \vdots \\ L_i(x, 1, N_i)\cos(\theta_1)\Delta\omega_1 & L_i(x, 2, N_i)\cos(\theta_2)\Delta\omega_2 & \ldots & L_i(x, m, N_i)\cos(\theta_m)\Delta\omega_m \end{pmatrix}^{-1}$$

$$\begin{pmatrix} L_o(x, k, 1) \\ L_o(x, k, 2) \\ \vdots \\ L_o(x, k, N_i) \end{pmatrix} \quad (7)$$

In this way, the reflection characteristics of the real object 21 can be estimated by using a light source matrix ($N_i * m$) determined based on the number of light source patterns ($N_i$) for the environment map information and the number of segmentation solid angles (m) formed by segmenting the environment map information, and the imaging information $L_o$ (1 to $N_i$) of the real object 21 irradiated with respective light source patterns. When $N_i = m$, a square light source matrix makes it possible to obtain a strict solution of the BRDF by using the inverse matrix of the light source matrix. On the other hand, a non-square light source matrix makes it possible to calculate a pseudo-inverse matrix by using Singular Value Deconfiguration (SVD). When $N_i > m$, an excessive determination makes it possible to obtain the least square solution of the BRDF. When $N_i < m$, a recessive determination makes it possible to obtain a minimum norm solution.

FIG. 4B is a conceptual view illustrating an example of segmentation solid angles according to the present exemplary embodiment.

Referring to FIG. 4B, the environment map 41 is segmented into m segmentation solid angles $\Delta\omega_j$ (j=1 to m). It is not necessary that all of the segmentation solid angles $\Delta\omega_j$ (j=1 to m) have the same magnitude. Referring to the formula (6), when the environment map 41 corresponds to a rendering formula for the first row of the matrix A, $L_i(x, 1, 1)$ corresponds to $L_i(1)$ illustrated in FIG. 4B, and likewise, $L_i(x, m, 1)$ corresponds to $L_i(m)$ illustrated in FIG. 4B. More specifically, $L_i(x, 1, 1)$ is equivalent to the radiation luminance of incident light to the point X on the real object 21 from the lighting direction ($\theta_1$, $\varphi_1$) at the segmentation solid angle $\Delta\omega_1$. Although, in FIG. 4B, the environment map is represented in the equirectangular projection format, the environment map may be represented in the equisolid angle projection or other formats.

(Operation Details)

The following describes detailed image processing of the image processing apparatus according to the present exemplary embodiment.

The following processing is implemented when the CPU 1 executes an image processing program.

[Estimation Processing of Reflection Characteristics of Real Object]

Figure 5:
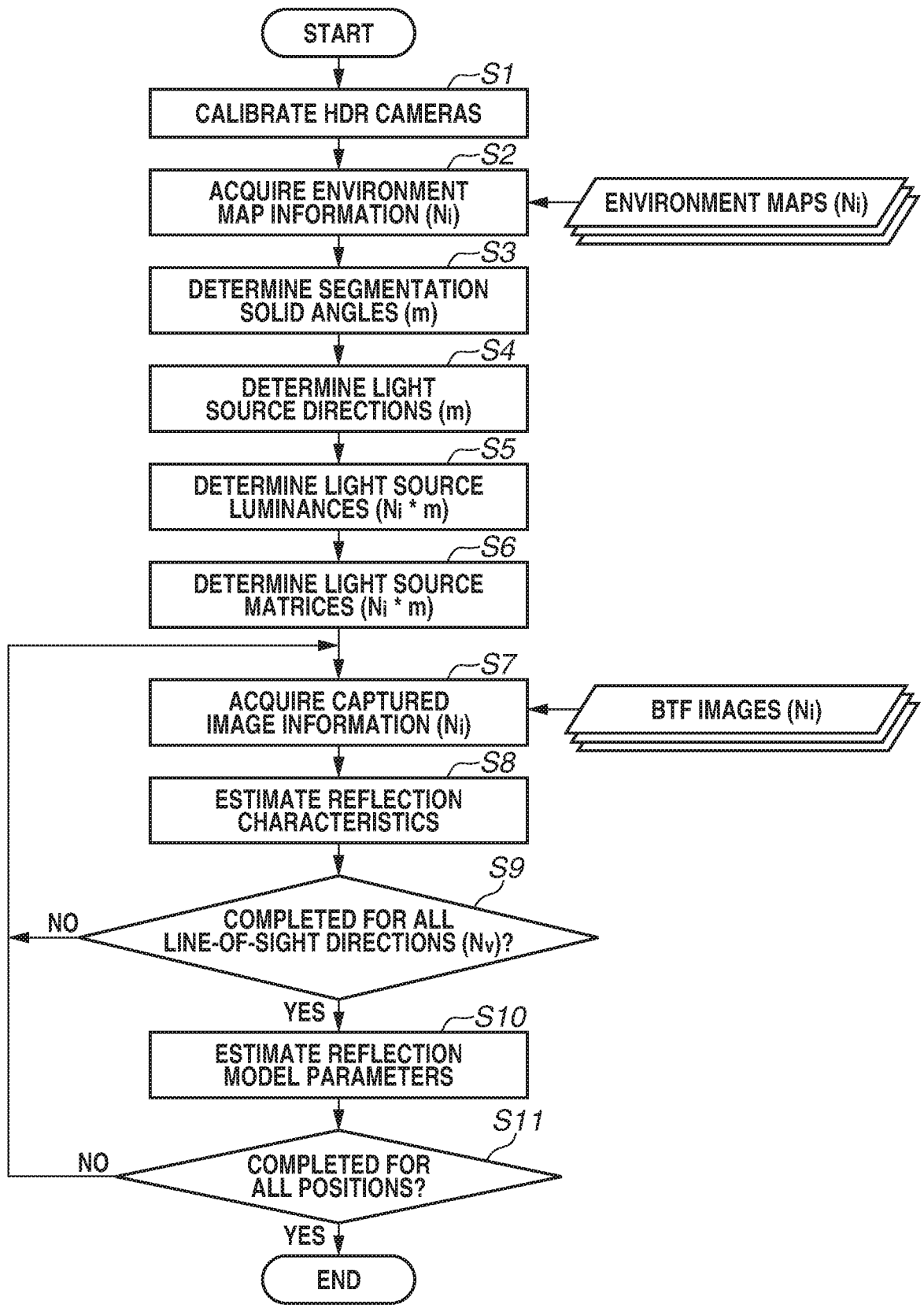
FIG. 5 is a flowchart illustrating estimation processing of reflection characteristics of a real object.

FIG. 5 is a flowchart illustrating estimation processing of reflection characteristics of the real object 21 according to the present exemplary embodiment. In step S1, the CPU 1 first performs HDR camera calibration processing to calibrate the omnidirectional camera 31 for acquiring the environment map information and the digital camera 23 for acquiring the captured image information. Since direct light from the light source 22 and specularly reflected light from the real object 21 have high luminance, a HDR camera may be used as the omnidirectional camera 31 and the digital camera 23. Pixel values of the captured image information (HDR images) captured by an HDR camera are associated with the radiation luminance [W/sr/m$^2$] (radiant quantity), the luminance [cd/m$^2$], or the tristimulus value XYZ [cd/m$^2$] (photometric quantity) through calibration.

In associating pixel values of HDR images with the radiant quantity and photometric quantity, for example, the technique discussed in "DEBEVEC P. E., MALIK J. 'Recovering high dynamic range radiance maps from photographs', In Proc. ACM SIGGRAPH 97 (August 1997), pp. 369-378" can be used. The technique discussed in "Kim, M., Kautz, J. 'Characterization for high dynamic range imaging', Eurographics 27(2), pp. 691-697 (2008)" can also be used.

In step S2, the CPU 1 performs environment map information acquisition processing to acquire environment maps for the $N_i$ light source patterns. The environment maps are acquired by performing HDR imaging on the $N_i$ light source patterns by using the omnidirectional camera 31 with a viewpoint set to the position of the point X on the real object 21. Instead of directly acquiring the environment maps, the CPU 1 may read omnidirectional HDR images captured and prestored as files in the HDD 5.

In step S3, the CPU 1 performs segmentation solid angle determination processing to segment each environment map into m segmentation solid angles $\Delta\omega_j$ (j=1 to m). More specifically, the CPU 1 estimates the reflection characteristics of a real object by segmenting each of a plurality of environment maps into a plurality of solid angles, and determining the lighting direction and light source luminance for each of the plurality of solid angles. There are two different cases of determining a segmentation solid angle allocation method. In one case, the method is predetermined based on the arrangement of light sources. In the other case, the method is automatically determined based on the environment maps for the $N_i$ light source patterns.

In the example illustrated in FIG. 2C, the segmentation solid angles are predetermined based on the arrangement of light sources. The light source 22 is arranged at the center of each triangle (or polygon) on the geodesic dome 26 so that a plurality of the light sources 22 is equally arranged over omnidirection. Although each triangle of the geodesic dome 26 is not strictly equirectangular, the segmentation solid angles can be approximated by segmenting the sphere (4π) or hemisphere (2π) of the entire solid angle by the number of triangles (m), i.e., $\Delta\omega_j$=4π/m or 2π/m [sr], respectively.

Although the segmentation solid angles can be easily calculated by using the allocation method, correct positioning when installing the light sources 22 is to be performed.

Figure 6A:
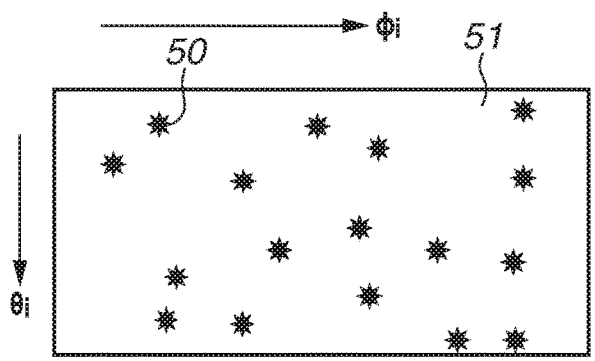
FIGS. 6A, 6B, and 6C illustrate an example of automatically determining segmentation solid angles based on the environment map information.
Figure 6B:
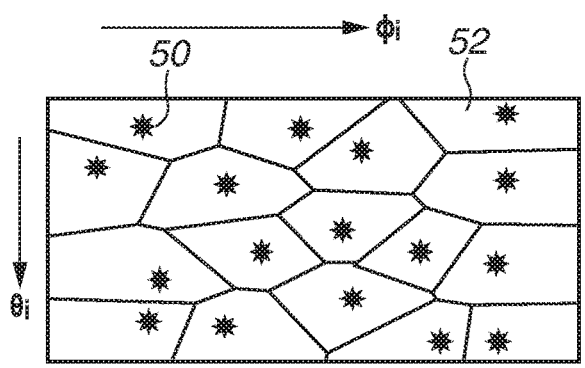
Figure 6C:
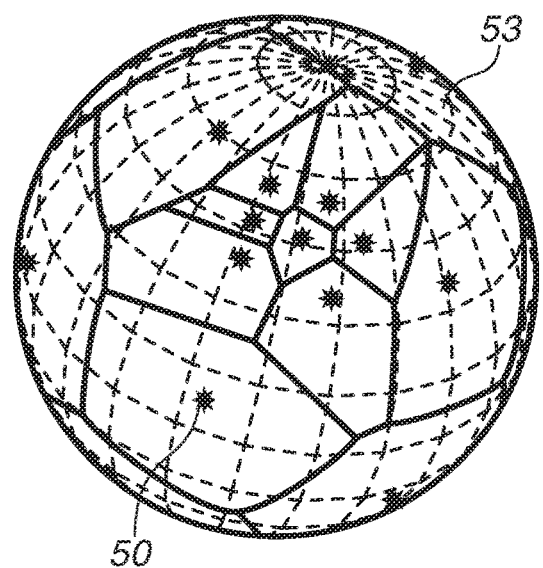

FIGS. 6A, 6B, and 6C illustrate an example of automatically determining segmentation solid angles based on environment maps for the $N_i$ light source patterns. According to the present exemplary embodiment, $N_i$ (=m) segmentation solid angles $\Delta\omega_j$ (j=1 to $N_i$) are determined for the $N_i$ light source patterns for simplicity. In each environment map of a light source pattern, the CPU 1 obtains a direction ($\theta_i$, $\varphi_i$) of a point 50 where the radiation luminance (or luminance) is maximized, and plots $N_i$ points where the radiation luminance (or luminance) is larger than a predetermined value on one omnidirectional image 51, as illustrated in FIG. 6A.

Then, as illustrated in FIG. 6B, the CPU 1 performs region segmentation based on a Voronoi diagram with the $N_i$ points, where the radiation luminance (or luminance) is larger than a predetermined value, set as kernel points. Segmentation regions 52 correspond to segmentation solid angles $\Delta\omega_j$ (j=1 to $N_i$). More specifically, the CPU 1 segments an environment map into a plurality of solid angles by performing region segmentation based on a Voronoi diagram with points, where the luminance in the environment map is larger than a predetermined value, set as kernel points. The Voronoi diagram refers to a diagram in which region segmentation is performed. More specifically, for a plurality of points (kernel points) arranged at arbitrary positions in a certain metric space, the region segmentation is performed depending on which kernel point other points in the same metric space are close to.

FIG. 6C three-dimensionally illustrates segmentation solid angles determined on an omnidirectional image composed of a segmentation solid angles $\Delta\omega$ 53 with different magnitudes. According to the present exemplary embodiment, the omnidirectional image 51 in the equirectangular projection format is used for simplicity. However, taking into consideration the accuracies of area calculation on segmentation solid angles and region segmentation, the above-described processing may be performed on an omnidirectional image in the equisolid angle projection format. In the equisolid angle projection format, the area on the image is proportional to the solid angle. Therefore, to obtain the magnitude of each segmentation solid angle $\Delta\omega$, the area of a region 52 formed by segmenting the area of the omnidirectional image as a sphere (4π) or hemisphere (2π) of the entire solid angle is to be obtained.

Although, in the Voronoi diagram illustrated in FIG. 6B, Voronoi boundaries are set at equidistant positions from each kernel point, weighting in the metric space may be changed in such a manner that the distance to a Voronoi boundary decreases as radiation luminance (or luminance) of each kernel point increases. Although, in the calculation of segmentation solid angles by using this allocation method, the area of each segmentation region on the omnidirectional image is to be obtained, the positions of the light sources 22 do not need to be regularly arranged.

In step S4, the CPU 1 performs lighting direction determination processing to determine the lighting direction ($\theta_i$, $\varphi_i$) of each segmentation solid angle $\Delta\omega_j$ (j=1 to m). There are two different methods of determining a lighting direction: one method uses the area center (gravity center), and the other method uses the luminance gravity center.

The area center (gravity center) is represented by the formula (8).

$$\theta_i = \frac{\int_{\Delta\omega} \theta_i d\omega_i}{\int_{\Delta\omega} d\omega_i} = \frac{\int_{\Delta\omega} \theta_i \sin\theta_i d\theta_i d\phi_i}{\int_{\Delta\omega} \sin\theta_i d\theta_i d\phi_i}$$
$$\phi_i = \frac{\int_{\Delta\omega} \phi_i d\omega_i}{\int_{\Delta\omega} d\omega_i} = \frac{\int_{\Delta\omega} \phi_i \sin\theta_i d\theta_i d\phi_i}{\int_{\Delta\omega} \sin\theta_i d\theta_i d\phi_i} \quad (8)$$

On the other hand, the luminance gravity center is represented by the formula (9).

$$\theta_i = \frac{\int_{\Delta\omega} L_i(x, d\omega_i)\theta_i d\omega_i}{\int_{\Delta\omega} L_i(x, d\omega_i) d\omega_i} = \frac{\int_{\Delta\omega} L_i(x, d\omega_i)\theta_i \sin\theta_i d\theta_i d\phi_i}{\int_{\Delta\omega} L_i(x, d\omega_i)\sin\theta_i d\theta_i d\phi_i}$$
$$\phi_i = \frac{\int_{\Delta\omega} L_i(x, d\omega_i)\phi_i d\omega_i}{\int_{\Delta\omega} L_i(x, d\omega_i) d\omega_i} = \frac{\int_{\Delta\omega} L_i(x, d\omega_i)\phi_i \sin\theta_i d\theta_i d\phi_i}{\int_{\Delta\omega} L_i(x, d\omega_i)\sin\theta_i d\theta_i d\phi_i} \quad (9)$$

Here, $L_i(x, d\omega_i)$ denotes the radiation luminance (or luminance) of each pixel within a segmentation solid angle.

In step S5, the CPU 1 performs light source luminance determination processing to obtain the average radiation luminance (or average luminance) of each segmentation solid angle $\Delta\omega_j$ (j=1 to m). The average radiation luminance (or average luminance) is represented by the formula (10).

$$L_i(x, \omega_i) = \frac{\int_{\Delta\omega} L_i(x, d\omega_i) d\omega_i}{\int_{\Delta\omega} d\omega_i} = \frac{\int_{\Delta\omega} L_i(x, d\omega_i)\sin\theta_i d\theta_i d\phi_i}{\int_{\Delta\omega} \sin\theta_i d\theta_i d\phi_i} \quad (10)$$

In step S6, the CPU 1 performs light source matrix determination processing to determine elements of the matrix A represented by the formula (7).

In an element $L_i(x, 1, 1)\cos(\theta_1) \Delta\omega_1$ of the matrix A, $L_i(x, 1, 1)$ is equivalent to the radiation luminance (or luminance) of incident light to the point X on the real object 21 from the lighting direction $(\theta_1, \varphi_1)$ at the segmentation solid angle $\Delta\omega_1$. $\theta_1$ is equivalent to the lighting direction at the segmentation solid angle $\Delta\omega_1$, and $\Delta\omega_1$ is equivalent to a segmentation solid angle. The CPU 1 substitutes for $\Delta\omega_1$ the magnitude [sr] of the solid angle $\Delta\omega_1$ obtained in the segmentation solid angle determination processing (step S3), and substitutes for $\theta_1$ the polar angle of the lighting direction $(\theta_i, \varphi_i)$ calculated by the formula (8) or (9) in the lighting direction determination processing (step S4). The CPU 1 substitutes for $L_i(x, 1, 1)$ the average radiation luminance [W/sr/m²] (or the average luminance [cd/m²]) calculated by the formula (10) in the light source luminance determination processing (step S5). The CPU 1 also obtains elements other than $L_i(x, 1, 1)\cos(\theta_1) \Delta\omega_1$ in a similar way to determine the light source matrix of the matrix A. Segmenting the environment maps into segmentation solid angles in this way enables reduction of the amount of calculation for the reflection characteristic estimation.

In step S7, the CPU 1 performs captured image information acquisition processing to image the real object 21 irradiated with the $N_i$ light source patterns to acquire Bidirectional Texture Function (BTF) images. These BTF images can be acquired by performing HDR imaging, by using the digital camera 23, on the real object 21 irradiated with the $N_i$ light source patterns. The CPU 1 acquires BTF images from the $N_v$ viewing directions in all steps. In this step, the CPU 1 acquires $N_i$ BTF images for one viewing direction ($k \in [1, N_v]$).

For simplicity, the present exemplary embodiment premises that the optical axis of the digital camera 23 coincides with the point X on the real object 21 and that the center pixel of each BTF image is a pixel in the viewing direction $(\theta_o, \varphi_o)$. The CPU 1 obtains the radiation luminance [W/sr/m²] (or the luminance [cd/m²]) of the center pixel of a BTF image as a pixel in the viewing direction $(\theta_o, \varphi_o)$ to acquire the imaging information $L_o$ (1 to $N_i$) represented by the formula (7). Instead of directly acquiring the BTF images, the CPU 1 may read HDR images captured and prestored as files in the HDD 5.

In step S8, the CPU 1 performs reflection characteristic estimation processing to estimate the reflection characteristics $f_r(x, 1, k)$ to $f_r(x, m, k)$ [1/sr]. More specifically, the CPU 1 substitutes in the formula (7) the light source matrix ($N_i$*m) determined in the light source matrix determination processing (step S6), and the imaging information $L_o$ (1 to $N_i$) in the viewing direction $(\theta_o, \varphi_o)$ acquired in the captured image information acquisition processing (step S7). The reflection characteristics $f_r(x, 1, k)$ to $f_r(x, m, k)$ represent the reflection characteristics for the m lighting directions (1 to m) and one viewing direction ($k \in [1, N_v]$). The reflection characteristics $f_r(x, 1, k)$ to $f_r(x, m, k)$ represent different reflection characteristics depending on the units of $L_i$ in the lighting direction and $L_o$ in the viewing direction. When the unit is the radiant quantity (or the radiation luminance [W/sr/m²]), $f_r(x, 1, k)$ to $f_r(x, m, k)$ represent the BRDF [1/sr]. When the unit is the photometric quantity (or the luminance [cd/m²]), $f_r(x, 1, k)$ to $f_r(x, m, k)$ represent the reflection characteristics [1/sr] based on the photometric quantity differently defined from the common BRDF. The latter reflection characteristics are referred to as Luminous BRDF [1/sr].

In step S9, the CPU 1 determines whether the processing in steps S7 and S8 is performed on the BTF images ($N_i$*$N_v$) in all viewing directions ($N_v$). When the processing is not completed for all viewing directions (NO in step S9), the CPU 1 repeats the processing in steps S7 and S8. On the other hand, when the processing is completed for all viewing directions (YES in step S9), the processing proceeds to step S10 (reflection model parameter estimation processing).

In step S10, the CPU 1 performs reflection model parameter estimation processing to estimate parameters of a reflection model of the real object 21. Although the reflection characteristics for all lighting directions (m) and all viewing directions ($N_v$) are discretely obtained through the processing before step S10, the reflection characteristics for an arbitrary lighting direction or viewing direction are not obtained.

Therefore, the CPU 1 performs fitting on the discrete reflection characteristics by using parameters of a Blinn-Phong reflection model, a Cook-Torrance reflection model, a Ward reflection model, and a Lafortune reflection model. This fitting enables the reflection characteristic estimation for an arbitrary lighting direction or viewing direction by using a reflection model, providing an effect of reducing the amount of reflection characteristic data.

In step S11, the CPU 1 determines whether the processing in steps S7 to S10 is completed for the positions of all points set on the real object 21. When the processing is not completed for all points (NO in step S11), the CPU 1 moves the point X on the real object 21 on the XYZ stage and repeats the processing in steps S7 to S10. There are two different methods for moving the point X: one method moves the real object 21, and the other method moves the light source 22 or the digital camera 23. On the other hand, when the processing is completed for all points (YES in step S11), the processing illustrated in FIG. 5 ends.

Effects of Present Exemplary Embodiment

As described above, with a viewpoint set to the position of an object, the image processing apparatus according to the present exemplary embodiment acquires, for each position of light sources, a plurality of environment maps obtained by extensively imaging the surrounding environment from the viewpoint. The image processing apparatus further acquires, for each of positions of the light sources, a plurality of captured images obtained by imaging from a plurality of directions the object irradiated with light from the light sources. Then, the image processing apparatus determines the reflection characteristics of the object based on the environment maps and a plurality of the captured images. This enables improvement of the estimation accuracy of the reflection characteristics of the real object by taking into consideration the influence of external light other than direct light and indirect light without providing restrictions in the measurement environment.

A second exemplary embodiment will be described below. According to the first exemplary embodiment, the reflection characteristics are estimated without taking into consideration the self-shading and self-shadowing by the real object 21 itself. However, since self-shading and self-shadowing may arise depending on the shape of the real object 21, an error may occur in the reflection characteristic estimation. Self-shading refers to a portion where incident light is intercepted, and self-shadowing refers to a portion where reflected light is intercepted. Therefore, the present exemplary embodiment estimates the reflection characteristics in consideration of self-shading and self-shadowing.

The first exemplary embodiment has been described above centering on a method of moving the real object 21 by using the XYZ stage and a method of moving the light source 22 and the digital camera 23 with the real object 21 fixed when estimating the reflection characteristics at the point X on the real object 21. The method is used to cause the point X on the real object 21 to coincide with a measurement point or cause a measurement point to coincide with the point X on the real object 21. The method premises that the viewpoint of the environment map and the optical axis direction of the digital camera 23 physically coincide with a measurement point.

The present exemplary embodiment will be described below centering on a method of virtually moving a measurement point and estimating the reflection characteristics at the point X on the real object 21 in such a manner that the real object 21, the light source 22, and the digital camera 23 are remained fixed.

Figure 7A:
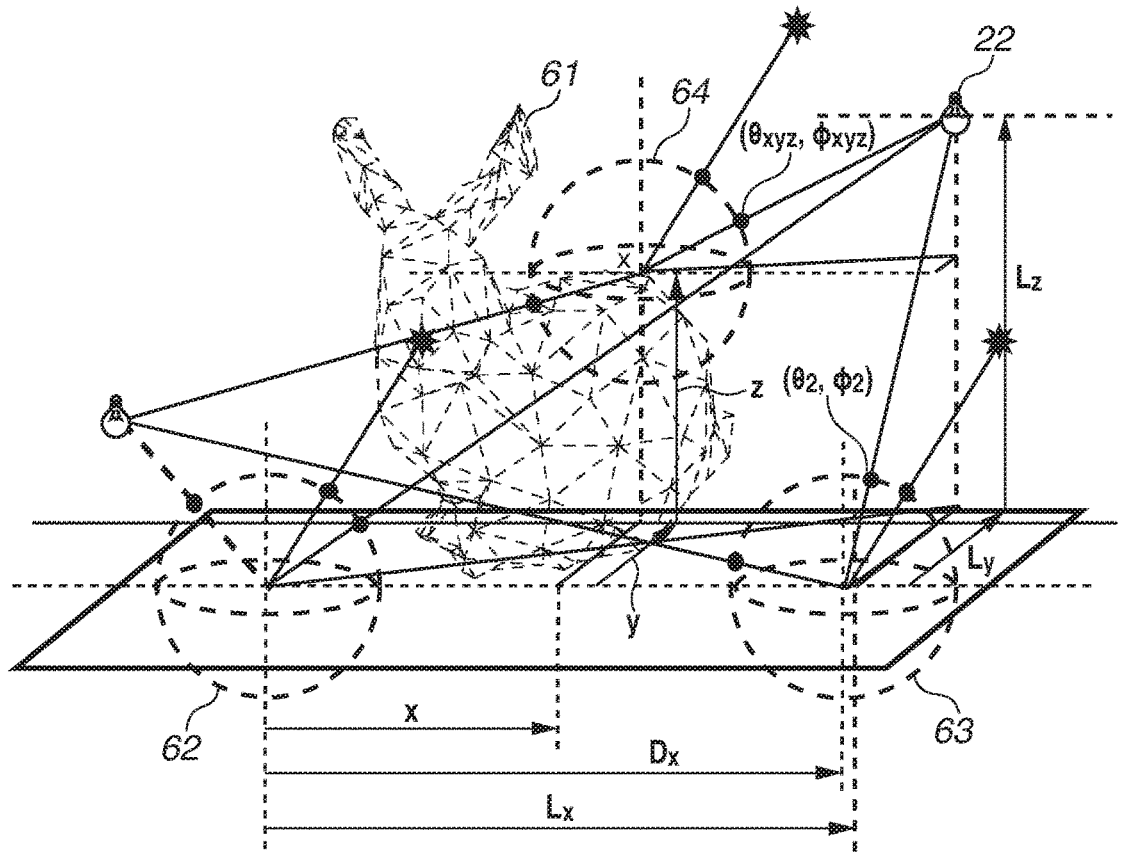
FIGS. 7A and 7B are conceptual views illustrating relations between environment map information and captured image information.
Figure 7B:
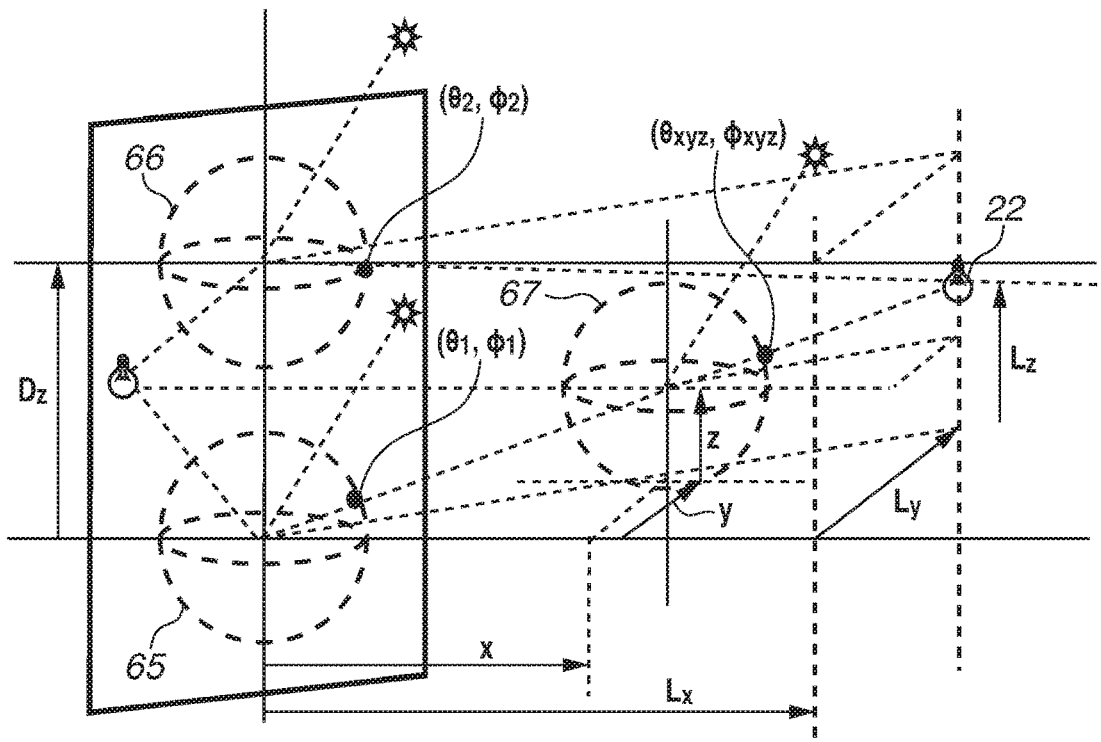
Figure 8:
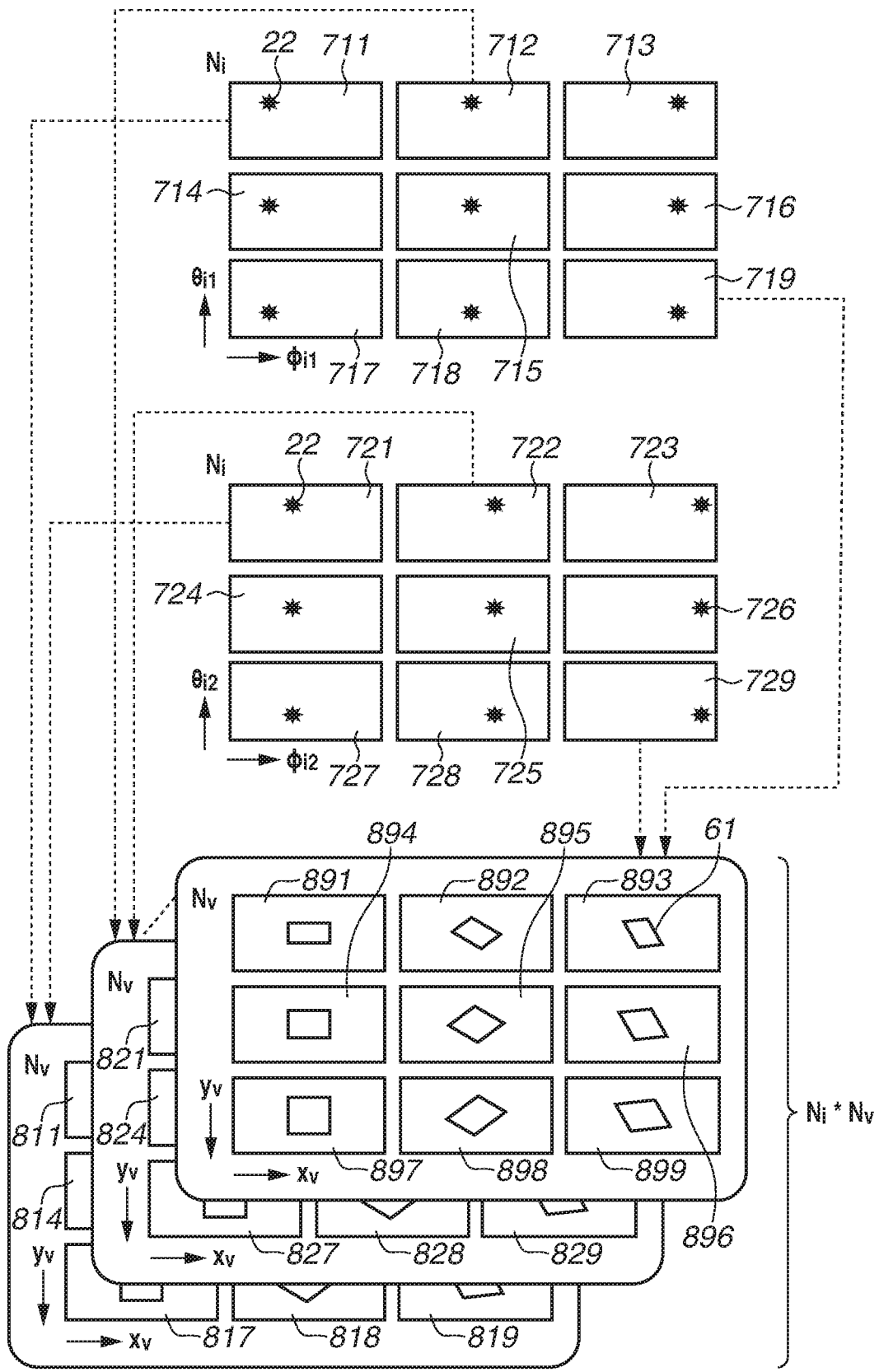
FIG. 8 is a conceptual view illustrating an example of generating virtual environment map information.

FIGS. 7A, 7B, and 8 are conceptual views illustrating relations between the environment map information and the captured image information, and an example of generating a virtual environment map according to the second exemplary embodiment. An example configuration of the image input device 13 (FIG. 2A) is identical to the configuration according to the first exemplary embodiment, and redundant descriptions thereof will be omitted. The present exemplary embodiment will be described in brief below centering on differences from the first exemplary embodiment.

(Environmental Map Information and Captured Image Information)

A relation between the environment map information and the captured image information according to the second exemplary embodiment will be described below.

FIG. 7A is a conceptual view illustrating an example of acquiring the environment map information according to the second exemplary embodiment.

According to the present exemplary embodiment, the image input device 13 can image, from arbitrary angles, a three-dimensional real object 61 irradiated with a light source pattern, while changing the light source pattern including direct light for irradiating the three-dimensional object 61 and indirect light. FIG. 7A illustrates an example of using a rabbit-shaped model as the real object 61. With the real object 61 having such a complicated shape, self-shading and self-shadowing may arise depending on the position of a point on the surface.

Similar to the first exemplary embodiment, the CPU 1 may acquire the environment map information 62 and 63 with a viewpoint set to a plurality of positions in a space, by using the omnidirectional camera 31 (FIG. 3A). More specifically, the CPU 1 acquires a plurality of environment maps with a viewpoint set to a plurality of positions on the real object 61. In this case, since an environment map includes a spherical or hemispherical light source pattern, the CPU 1 may acquire environment maps by using a camera with a fish-eye lens or a mirror ball instead of the omnidirectional camera 31. The CPU 1 generates virtual environment map information 64 (described in detail below) with a viewpoint set to the position of the point X on the three-dimensional real object 61, by using the acquired environment map information 62 and 63. In this case, the environment map information with a viewpoint set to a plurality of positions in a space does not need to be limited to two in number and may be three or more.

According to the present exemplary embodiment, with regard to light source patterns for 9 different lighting directions, the CPU 1 acquires environment maps 711 to 719 at the position of the environment map information 62, and acquire environment maps 721 to 729 at the position of the environment map information 63.

FIG. 8 illustrates correspondence relations between the environment maps 711 to 719 acquired at the position of the environment map information 62 and the environment maps 721 to 729 acquired at the position of the environment map information 63, and captured images 811 to 899 captured from 9 different viewing directions for each light source pattern.

The number of lighting directions and the number of viewing directions do not need to be limited to 9. With the $N_i$ light source patterns and the $N_v$ viewing directions, the number of environment maps acquired at each of the positions of the environment map information 62 and 63 is $N_i$ and the total number of captured images is given by $N_i * N_v$. In this case, the environment maps are omnidirectional images. For example, the environment maps acquired at the position of the environment map information 62 are represented in the equirectangular projection format with a vertical axis $\theta_{i1}$ and a horizontal axis $\varphi_{i1}$, and the environment maps acquired at the position of the environment map information 63 are represented in the equirectangular projection format with a vertical axis $\varphi_{i2}$ and a horizontal axis $\theta_{i2}$. $\theta_{i1}$ and $\theta_{i2}$ are polar angles, and $\varphi_{i1}$ and $\varphi_{i2}$ are azimuth angles. The captured images are represented with a horizontal axis $x_v$ [pixel] and a vertical axis $y_v$ [pixel]. For example, if the optical axis of the digital camera 23 coincides with the origin of the three-dimensional global coordinate (or world coordinate) system for the real object 61 and the stage on which the real object 61 is placed, the center pixel of each captured image is represented by ($\theta_c$, $\varphi_c$).

(Generating Virtual Environment Map)

The following describes an example of generating a virtual environment map according to the second exemplary embodiment.

As illustrated in FIG. 7A, the CPU 1 generates virtual environment map information 64 with a viewpoint set to the position of the point X on the three-dimensional real object 61 based on the environment map information 62 and 63 with a viewpoint set to a plurality of positions in a space.

The CPU 1 first acquires the environment maps 711 and 721 at the positions of the environment map information 62 and 63, respectively, which are $D_x$ [m] distant in the x-axis direction.

Then, the CPU 1 searches for corresponding points in the two omnidirectional images, i.e., the environment maps 711 and 721 acquired at the positions of the environment map information 62 and 63, respectively. Known techniques such as Scale-Invariant Feature Transform (SIFT) can be used for corresponding point search.

Then, based on information about the corresponding points in the two omnidirectional images, the CPU 1 generates a virtual environment map at the position (virtual position) of the virtual environment map information 64.

For example, when corresponding points for the light source 22 are found on the environment maps 711 and 721, the corresponding points on the environment maps 711 and 721 have the coordinates ($\theta_1$, $\varphi_1$) and ($\theta_2$, $\varphi_2$), respectively.

When the position of the environment map information 62 is set as reference coordinates (0, 0, 0), the coordinates ($\theta_{xyz}$, $\varphi_{xyz}$) of the corresponding points on the virtual environment map with a viewpoint set to the position (x, y, z) of the virtual environment map information 64 can be calculated as follows. When the position of the environment map information 63 has the coordinates ($D_x$, 0, 0) and the position of the light source 22 has the coordinates ($L_x$, $L_y$, $L_z$), relations between the azimuth angles $\varphi_1$, $\varphi_2$, and $\varphi_{xyz}$ of respective environment maps can be represented by the formula (11).

$$\left.\begin{array}{l} \tan\phi_1 = \dfrac{L_y}{L_x} \\ \tan\phi_2 = \dfrac{L_y}{L_x - D_x} \\ \tan\phi_{xyz} = \dfrac{L_y - y}{L_x - x} \end{array}\right\} \quad (11)$$

Solving the first and the second expressions of the formula (11) for $L_x$ and $L_y$ gives the formula (12).

$$\left.\begin{array}{l} L_x = \dfrac{D_x \tan\phi_2}{\tan\phi_2 - \tan\phi_1} \\ L_y = \dfrac{D_x \tan\phi_1 \tan\phi_2}{\tan\phi_2 - \tan\phi_1} \end{array}\right\} \quad (12)$$

Substituting the formula (12) for the third expression of the formula (11) and making arrangements give the formula (13).

$$\tan\phi_{xyz} = \dfrac{D_x \tan\phi_1 \tan\phi_2 - y(\tan\phi_2 - \tan\phi_1)}{D_x \tan\phi_2 - x(\tan\phi_2 - \tan\phi_1)} \quad (13)$$

Based on the formula (13), an azimuth angle $\varphi_{xyz}$ of the corresponding point on the virtual environment map with a viewpoint set to the position (x, y, z) can be determined by the azimuth angle $\varphi_1$ of the corresponding point on the environment map 711 and the azimuth angle $\varphi_2$ of the corresponding point on the environment map 721, and the interval distance $D_x$ [m] between the environment map information 62 and 63. On the other hand, when the formula (11) is rearranged, the polar angles $\theta_1$, $\theta_2$, and $\theta_{xyz}$ of respective environment maps can be represented by the formula (14).

$$\left.\begin{array}{l} \tan\theta_1 = \dfrac{\sqrt{L_x^2 + L_y^2}}{L_z} = \dfrac{\sqrt{L_x^2 + L_x^2\tan^2\phi_1}}{L_z} = \dfrac{L_x}{L_z}\sec\phi_1 \\ \tan\theta_2 = \dfrac{\sqrt{(L_x - D_x)^2 + L_y^2}}{L_z} = \dfrac{\sqrt{\dfrac{(L_x - D_x)^2 + (L_x - D_x)^2}{\tan^2\phi_2}}}{L_z} = \dfrac{L_x - D_x}{L_z}\sec\phi_2 \\ \tan\theta_{xyz} = \dfrac{\sqrt{(L_x - x)^2 + (L_y - y)^2}}{L_z - z} = \dfrac{\sqrt{\dfrac{(L_x - x)^2 + (L_x - x)^2}{\tan^2\phi_{xyz}}}}{L_z - z} = \dfrac{L_x - x}{L_z - z}\sec\phi_{xyz} \end{array}\right\} \quad (14)$$

Solving the first and the second expressions of the formula (14) and the formula (11) for $L_x$, $L_y$, and $L_z$ gives the formula (15).

$$\left.\begin{array}{l} L_x = L_z \tan\theta_1 \cos\phi_1 \\ L_y = L_x \tan\phi_1 = L_z \tan\theta_1 \sin\phi_1 \\ L_z = \dfrac{D_x}{\tan\theta_1 \cos\phi_1 - \tan\theta_2 \cos\phi_2} \end{array}\right\} \quad (15)$$

Substituting the formula (15) for the third expression of the formula (14) and making arrangements give the formula (16).

$$\tan\theta_{xyz} = \dfrac{D_x \tan\theta_1 \cos\phi_1 - x(\tan\theta_1 \cos\phi_1 - \tan\theta_2 \cos\phi_2)}{D_x - z(\tan\theta_1 \cos\phi_1 - \tan\theta_2 \cos\phi_2)} \cdot \sec\phi_{xyz} \quad (16)$$

-continued $$= \frac{x(\tan\theta_1\cos\phi_1 - \tan\theta_2\cos\phi_2)}{D_x - z(\tan\theta_1\cos\phi_1 - \tan\theta_2\cos\phi_2)} \cdot$$

$$\sec\left(\tan^{-1}\frac{D_x\tan\phi_1\tan\phi_2 - y(\tan\phi_2 - \tan\phi_1)}{D_x\tan\phi_2 - x(\tan\phi_2 - \tan\phi_1)}\right)$$

Based on the formula (16), the polar angle $\theta_{xyz}$ of the corresponding point on the virtual environment map with a viewpoint set to the position (x, y, z) can be determined by the coordinates ($\theta_1$, $\varphi_1$) of the corresponding point on the environment map 711, the coordinates ($\theta_2$, $\varphi_2$) of the corresponding point on the environment map 721, and the interval distance $D_x$ [m] between the two coordinates.

Then, the CPU 1 determines the coordinates ($\theta_{xyz}$, $\varphi_{xyz}$) of the corresponding point on the virtual environment map by using the formulas (13) and (16). For example, the CPU 1 calculates an average pixel value based on the pixel values of the corresponding points ($\theta_1$, $\varphi_1$) and ($\theta_2$, $\varphi_2$) on the environment maps 711 and 721, respectively. Then, the CPU 1 determines the pixel value of the corresponding point ($\theta_{xyz}$, $\varphi_{xyz}$) on the virtual environment map.

The CPU 1 plots all corresponding points on the virtual environment map for the environment map information 62 and 63 to enable generating a virtual environment map with a viewpoint set to the position (x, y, z) in a space. More specifically, the CPU 1 can generate a virtual environment map with a viewpoint set to the position of an arbitrary point X on the three-dimensional real object 61.

However, since occlusion actually occurs, there arises a case where no corresponding points are found. In such a case, occlusion can be avoided by changing the position of the environment map information.

More specifically, when avoiding occlusion, the CPU 1 generates virtual environment map information 67 with a viewpoint set to the position of the point X on the three-dimensional real object 61, based on environment map information 65 and 66 with a viewpoint set to a plurality of positions in a space different from the space illustrated in FIG. 7A, as illustrated in FIG. 7B. For more details, the CPU 1 first acquires the environment maps 711 and 721 at the positions of the environment map information 65 and 66, respectively, which are Dz [m] distant in the z-axis direction.

Then, the CPU 1 searches for corresponding points in the two omnidirectional images, i.e., the environment maps 711 and 721 acquired at the positions of the environment map information 65 and 66, respectively.

Then, based on information about the corresponding points in the two omnidirectional images, the CPU 1 generates a virtual environment map at the position of the virtual environment map information 67.

For example, when corresponding points for the light source 22 are found on the environment maps 711 and 721, the corresponding point on the environment map 711 has the coordinates ($\theta_1$, $\varphi_1$), and the corresponding point on the environment map 721 has the coordinates ($\theta_2$, $\varphi_2$). When the position of the environment map information 65 is set as reference coordinates (0, 0, 0), the coordinates ($\theta_{xyz}$, $\varphi_{xyz}$) of the corresponding point on the virtual environment map with a viewpoint set to the position (x, y, z) of the virtual environment map information 67 can be calculated as follows. When the position of the environment map information 66 has the coordinates (0, 0, Dz) and the position of the light source 22 has the coordinates ($L_x$, $L_y$, $L_z$), the azimuth angles $\varphi_1$, $\varphi_2$, and $\varphi_{xyz}$ of respective environment maps can be represented by the formula (17).

$$\left.\begin{array}{l}\tan\phi_1 = \tan\phi_2 = \dfrac{L_y}{L_x} \\[6pt] \tan\phi_{xyz} = \dfrac{L_y - y}{L_x - x}\end{array}\right\} \quad (17)$$

On the other hand, when the formula (17) is rearranged, the polar angles $\theta_1$, $\theta_2$, and $\theta_{xyz}$ of respective environment maps can be represented by the formula (18).

$$\left.\begin{array}{l}\tan\theta_1 = \dfrac{\sqrt{L_x^2 + L_y^2}}{L_z} = \dfrac{\sqrt{L_x^2 + L_x^2\tan^2\phi_1}}{L_z} = \dfrac{L_x}{L_z}\sec\phi_1 \\[10pt] \tan\theta_2 = \dfrac{\sqrt{L_x^2 + L_y^2}}{L_z - D_z} = \dfrac{\sqrt{L_x^2 + L_x^2 + \tan^2\phi_1}}{L_z} = \dfrac{L_x}{L_z - D_z}\sec\phi_1 \\[10pt] \tan\theta_{xyz} = \dfrac{\sqrt{(L_x - x)^2 + (L_y - y)^2}}{L_z - z} = \dfrac{\sqrt{\dfrac{(L_x - x)^2 + (L_x - x)^2}{\tan^2\phi_{xyz}}}}{L_z - z} = \dfrac{L_x - x}{L_z - z}\sec\phi_{xyz}\end{array}\right\} \quad (18)$$

When $L_x$ and $L_y$ are calculated by using the first expression of the formula (18) and the first expression of the formula (17) and then substituted for the second expression of the formula (18) to calculate $L_z$, the formula (19) is given.

$$\left.\begin{array}{l}L_x = L_z\tan\theta_1\cos\phi_1 \\[4pt] L_y = L_x\tan\phi_1 = L_z\tan\theta_1\sin\phi_1 \\[4pt] L_z = \dfrac{D_z\tan\theta_2}{\tan\theta_2 - \tan\theta_1}\end{array}\right\} \quad (19)$$

Substituting the formula (19) for the second expression of the formula (17) and making arrangements give the formula (20).

$$\begin{aligned}\tan\theta_{xyz} &= \frac{L_x\tan\phi_1 - y}{L_x - x} \\ &= \frac{L_z\tan\theta_1\sin\phi_1 - y}{L_z\tan\theta_1\cos\phi_1 - x} \\ &= \frac{D_z\tan\theta_1\tan\theta_2\sin\phi_1 - y(\tan\theta_1 - \tan\theta_2)}{D_z\tan\theta_1\tan\theta_2\cos\phi_1 - x(\tan\theta_1 - \tan\theta_2)}\end{aligned} \quad (20)$$

Substituting the formula (19) for the third expression of the formula (18) and making arrangements give the formula (21).

$$\tan\theta_{xyz} = \frac{D_z\tan\theta_1\tan\theta_2\cos\phi_1 - x(\tan\theta_2 - \tan\theta_2)}{D_z\tan\theta_2 - z(\tan\theta_2 - \tan\theta_1)} \cdot \sec\phi_{xyz} \quad (21)$$

$$= \frac{D_z\tan\theta_1\tan\theta_2\cos\phi_1 - x(\tan\theta_2 - \tan\theta_1)}{D_z\tan\theta_2 - z(\tan\theta_2 - \tan\theta_1)} \cdot$$

$$\sec\left(\tan^{-1}\frac{D_z\tan\phi_1\tan\phi_2\sin\phi_1 - y(\tan\phi_2 - \tan\phi_1)}{D_z\tan\phi_1\tan\phi_2\cos\phi_1 - x(\tan\phi_2 - \tan\phi_1)}\right)$$

Based on the formulas (20) and (21), the coordinates ($\theta_{xyz}$, $\varphi_{xyz}$) of the corresponding point on the virtual environment map with a viewpoint set to the position (x, y, z) can be determined by the coordinates ($\theta_1$, $\varphi_1$) and ($\theta_2$, $\varphi_2$) of the corresponding point of concern on the environment maps 711 and 712, respectively, and an interval distance Dz [m] between the two coordinates.

For example, the CPU 1 calculates an average pixel value based on the pixel values of the corresponding points ($\theta_1$, $\varphi_1$) and ($\theta_2$, $\varphi_2$) on the environment maps 711 and 721, respectively. Then, the CPU 1 determines the pixel value of the corresponding point ($\theta_{xyz}$, $\varphi_{xyz}$) on the virtual environment map. Further, similar to the case where the environment map information 62 and 63 is used, the CPU 1 plots all corresponding points on the virtual environment map for the environment map information 65 and 66 to generate a virtual environment map with a viewpoint set to the position (x, y, z) in a space. More specifically, by optimally arranging the positions of a plurality of pieces of environment map information, the CPU 1 can generate a virtual environment map with a viewpoint set to the position of an arbitrary point X on the three-dimensional real object 61 while avoiding occlusion.

Figure 9A:
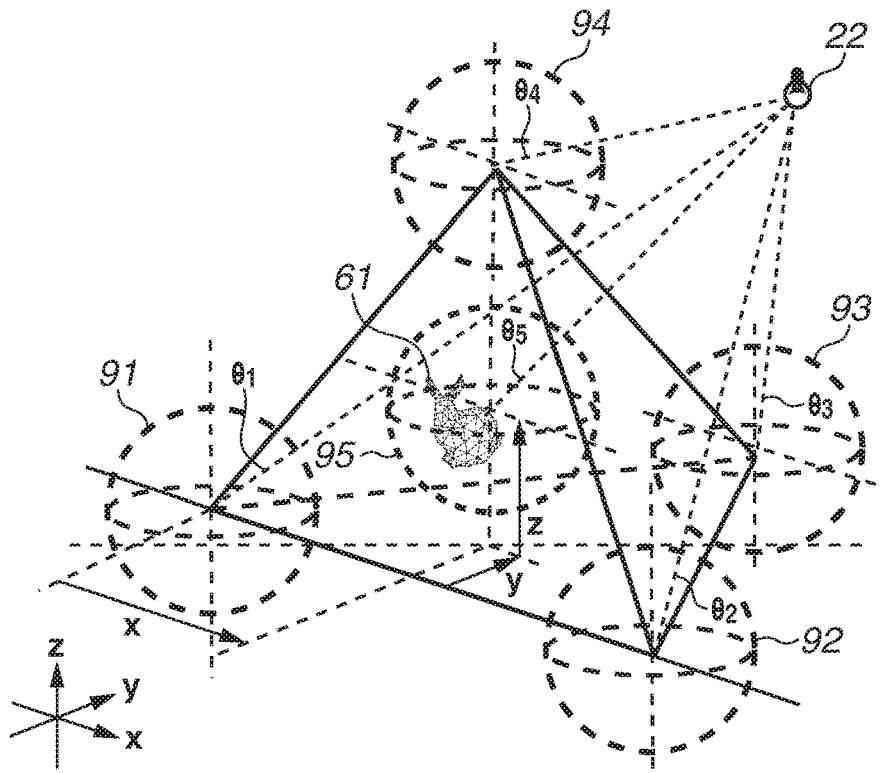
FIGS. 9A and 9B illustrate examples of three-dimensional optimal arrangements of a plurality of pieces of environment map information.
Figure 9B:
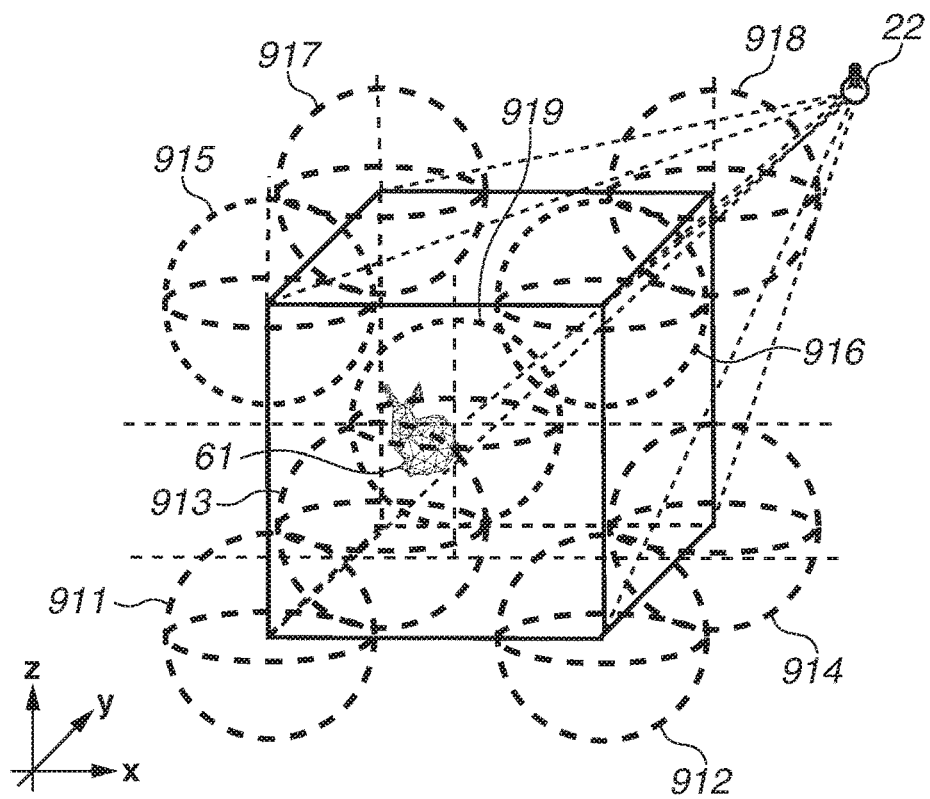

FIGS. 9A and 9B illustrate examples of three-dimensional optimal arrangements of a plurality of pieces of environment map information according to the second exemplary embodiment.

FIG. 9A illustrates an example of generating virtual environment map information 95 based on environment map information 91 to 94 for four different points which encompass the three-dimensional real object 61. If corresponding points are found in the environment map information for at least two out of four points, the CPU 1 can determine the coordinates of corresponding points on the virtual environment map. If corresponding points are found in the environment map information for three or more points, the reliability can be further improved based on relations among a plurality of corresponding points.

Likewise, as illustrated in FIG. 9B, the CPU 1 may generate virtual environment map information 919 based on environment maps 911 to 918 for 8 points which encompass the three-dimensional real object 61.

(Processing for Estimating Reflection Characteristics of Real Object)

Figure 10:
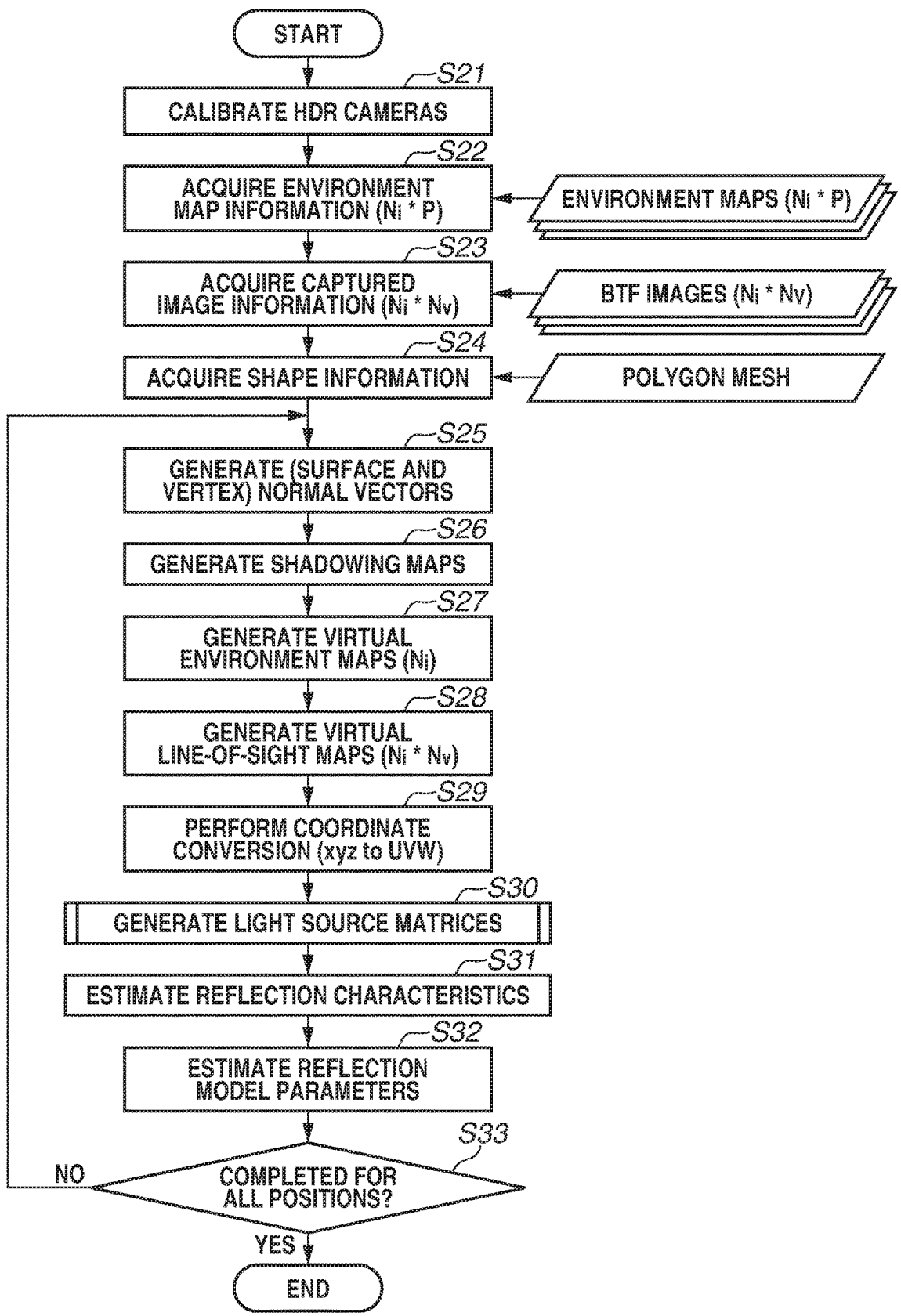
FIG. 10 is a flowchart illustrating estimation processing of reflection characteristics of a three-dimensional real object.

FIG. 10 is a flowchart illustrating estimation processing of reflection characteristics of a three-dimensional real object according to the present exemplary embodiment. The present exemplary embodiment will be described in brief below centering on differences from the first exemplary embodiment.

FIG. 10 is a flowchart illustrating an example of estimation processing of reflection characteristics of a three-dimensional real object.

In step S21, similar to step S1 illustrated in FIG. 5, the CPU 1 first performs HDR camera calibration processing to calibrate the omnidirectional camera 31 for acquiring the environment map information and the digital camera 23 for acquiring the captured image information.

In step S22, the CPU 1 performs environment map information acquisition processing to acquire environment maps for the $N_i$ light source patterns from the positions of environment map information for P points. The environment maps are acquired by performing HDR imaging on the $N_i$ light source patterns by using the omnidirectional camera 31 with a viewpoint set to the positions of the P points. Instead of directly acquiring the environment maps, the CPU 1 may read omnidirectional HDR images captured in advance, from the HDD 5.

In step S23, the CPU 1 performs captured image information acquisition processing to image the three-dimensional real object 61 irradiated with the $N_i$ light source patterns to acquire BTF images. The CPU 1 acquires the BTF images by performing, from the $N_v$ viewing directions by using the digital camera 23, HDR imaging ($N_i*N_v$) on the real object 61 irradiated with the $N_i$ light source patterns. For simplicity, the present exemplary embodiment premises that the optical axis of the digital camera 23 which performs imaging from the $N_v$ viewing directions coincides with the origin of the global coordinate system for the stage on which the three-dimensional real object 61 is placed, and that the center pixel of a captured image is a pixel in the viewing direction ($\theta_c$, $\varphi_c$). Instead of directly acquiring BTF images, the CPU 1 may also read HDR images captured in advance, from the HDD 5.

In step S24, the CPU 1 performs shape information acquisition processing to acquire a polygon mesh of the three-dimensional real object 61. The shape of the three-dimensional real object 61 is measured by using such a known technique as a 3D laser scanner, a photometric stereo, stereovision, or visual hull, and represented by three-dimensional coordinates of a point group or polygon mesh. For simplicity, a point group is assumed to be reconfigured into a polygon mesh. Instead of directly acquiring three-dimensional shapes, the CPU 1 may also read a polygon mesh measured in advance, from the HDD 5. In this case, the three-dimensional coordinates of the shape of the three-dimensional real object 61 are based on the local coordinate (or object coordinate or body coordinate) system, and therefore are to be converted into those of the global coordinate system for the stage on which the three-dimensional real object 61 is placed.

In step S25, the CPU 1 performs normal vector generation processing to generate a surface normal vector or vertex normal vector at the point X on the three-dimensional real object 61 from the polygon mesh. The surface normal vector, a unit vector perpendicular to the surface of the polygon plane, can be obtained by using the three-dimensional coordinates and the outer product of the vertexes of the polygon including the point X on the three-dimensional real object 61. On the other hand, the vertex normal vector can be obtained by adding all of surface normal vectors of the polygons which share the vertexes of the polygon including the point X on the three-dimensional real object 61 and performing normalization.

In this case, each normal vector in the global coordinate system can be represented by ($n_x$, $n_y$, $n_z$).

In step S26, the CPU 1 performs shadowing map generation processing to generate a shadowing map at the point X on the three-dimensional real object 61. In the shadowing map generation processing (step S26), the CPU 1 may generate a visible map instead of the shadowing map. The shadowing map will be described below.

If surface unevenness can be ignored like the real object 21 according to the first exemplary embodiment, self-shading and self-shadowing do not largely affect processing. On the other hand, if geometric surface unevenness cannot be ignored like the three-dimensional real object 61, the reflection characteristics in consideration of the influences of self-shading and self-shadowing are to be estimated. This is because the definition of the reflection characteristics such as a BRDF premises that neither self-shading nor self-shadowing exists in the relation between incident light and reflected light. Therefore, the present exemplary embodiment estimates the reflection characteristics of the real object by generating a shadowing map indicating whether incident light to the real object 61 is shadowed and applying the generated shadowing map to the environment map, based on shape information for the real object 61.

Figure 11A:
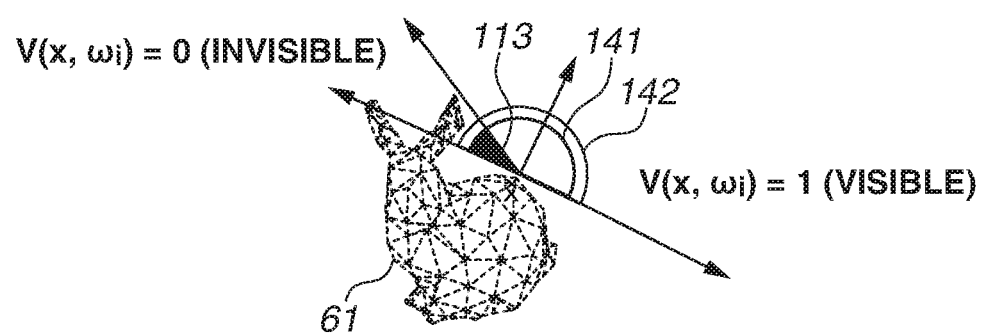
FIGS. 11A and 11B are conceptual views illustrating an example of generating a shadowing map.
Figure 11B:
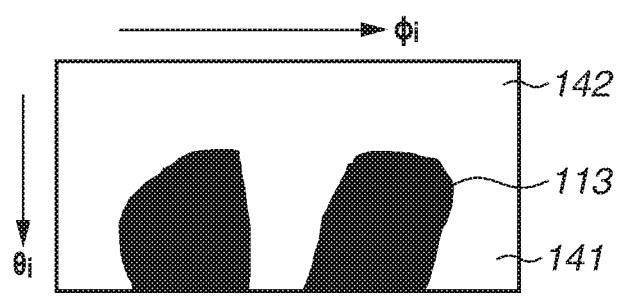

FIGS. 11A and 11B are conceptual views illustrating an example of generating a shadowing map. The shadowing map represents whether incident light is intercepted in the form of an omnidirectional image with a viewpoint set to the position of the point X on the three-dimensional real object 61.

When estimating the reflection characteristics at the point X on the three-dimensional real object 61, the CPU 1 uses a hemispherical shadowing map 142 with a viewpoint set to the position of the point X on the three-dimensional real object 61, as illustrated in FIG. 11A. In this case, the hemisphere is determined by the zenith and the tangent plane on the normal vector. Further, when estimating also transmission characteristics at the point X on the three-dimensional real object 61, the CPU 1 uses a spherical shadowing map with a viewpoint set to the position of the point X on the three-dimensional real object 61. This shadowing map includes information indicating self-shading or self-shadowing at a point on the real object 61.

The CPU 1 generates a shadowing map by determining whether the polygon mesh of the three-dimensional real object 61 intersects with the straight line from the point X on the three-dimensional real object to the lighting direction $\omega_i$. When the polygon mesh intersects with the straight line (shadowed), the CPU 1 sets the pixel value of the omnidirectional image to 0. On the other hand, when the polygon mesh does not intersect with the straight line (not shadowed), the CPU 1 sets the pixel value to 1. Referring to FIG. 11A, the real object (rabbit) is segmented into shadowed portions 113 (invisible region) shadowed by ear portions and an unshadowed portion 141 (visible region). More specifically, the shadowing map includes information indicating a visible region. In the case of transmission characteristics, the shadowed portions 113 are transmitting portions.

When the shadowing map is expressed as a visible function $V(x, \omega_i)$, the function can be represented by the formula (22).

$$V(x, \omega_i) = \begin{cases} 0 \\ 1 \end{cases} \quad (22)$$

Here, $V(x, \omega_i)$ for the lighting direction $\omega_i$ represents self-shading and $V(x, \omega_r)$ for the viewing direction represents self-shadowing.

FIG. 11B illustrates an example of a generated hemispheric shadowing map. In an omnidirectional image 142 with a viewpoint set to the position of the point X on the three-dimensional real object 61, ear portions of the rabbit (real object 61) are expressed as self-shading 113.

In step S27, the CPU 1 performs virtual environment map generation processing to generate a virtual environment map with a viewpoint set to the position of the point X on the three-dimensional real object 61.

FIGS. 12A to 13C are conceptual views illustrating relations among a normal vector, a virtual environment map, and a shadowing map according to the second exemplary embodiment. When estimating the reflection characteristics at the point X on the three-dimensional real object 61, the CPU 1 uses a hemispheric virtual environment map with a viewpoint set to the position of the point X on the three-dimensional real object 61 in a similar way to the shadowing map. More specifically, based on the information indicating a visible region in the shadowing map, the CPU 1 generates a virtual environment map and a virtual line-of-sight map at a virtual position.

In this case, the hemisphere is determined by the zenith and the tangent plane on the normal vector. Further, when estimating also transmission characteristics at the point X on the three-dimensional real object 61, the CPU 1 uses a spherical virtual environment map with a viewpoint set to the position of the point X on the three-dimensional real object 61. The CPU 1 generates a spherical or hemispherical virtual environment map with a viewpoint set to the position of the point X on the three-dimensional real object 61 according to the above-described virtual environment map generation method by using the environment map information for the P points acquired in the environment map information acquisition processing (step S22).

Figure 12A:
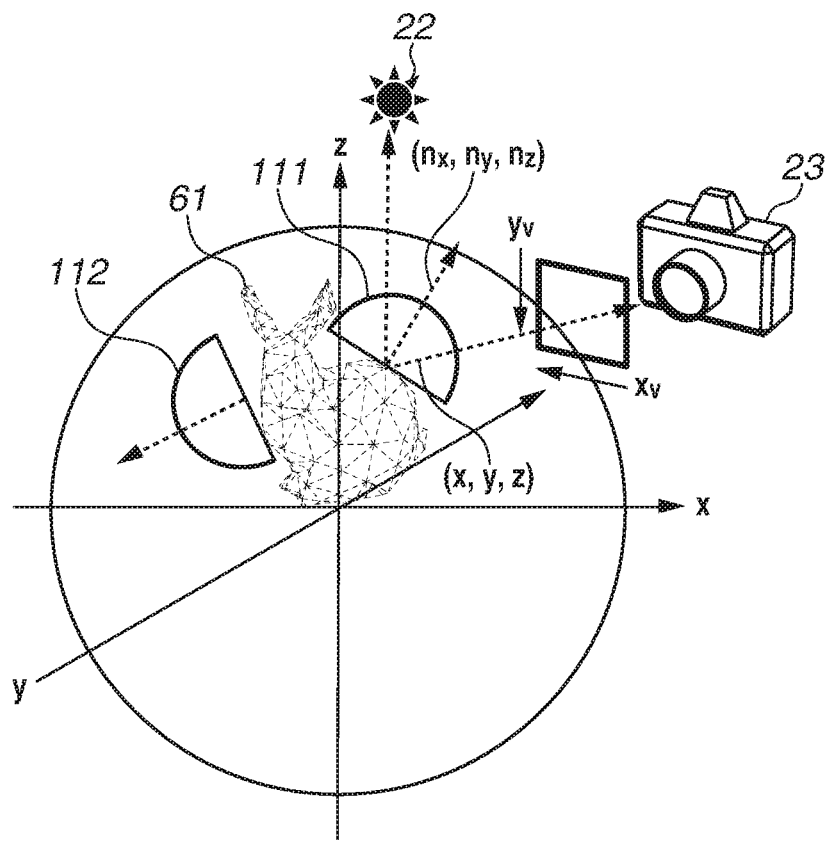
FIGS. 12A and 12B are conceptual views illustrating a relation between a normal vector and a virtual environment map.

FIG. 12A is a conceptual view illustrating a relation between a normal vector for the coordinates (x, y, z) of the point X on the three-dimensional real object 61 and a virtual environment map. The three-dimensional coordinates of the polygon mesh of the three-dimensional real object 61 are defined with the global coordinate system, and the normal vector for the coordinates (x, y, z) of the point X on the three-dimensional real object 61 is represented by $(n_x, n_y, n_z)$. Reflection characteristics at the point X on the three-dimensional real object 61 can be obtained by using a hemispheric virtual environment map 111 with a viewpoint set to the coordinates (x, y, z). A hemispheric virtual environment map 112 is an example of a hemispheric virtual environment map with a viewpoint set to the position of another point X on the three-dimensional real object 61.

Figure 12B:
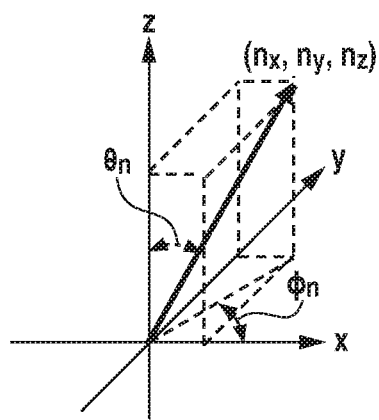

FIG. 12B illustrates a normal vector $(n_x, n_y, n_z)$ in the global coordinate system. The polar angle $\theta_n$ and the azimuth angle $\varphi_n$ of the normal vector $(n_x, n_y, n_z)$ can be represented by the formula (23).

$$\begin{aligned} \theta_n &= \tan^{-1} \frac{\sqrt{n_x^2 + n_y^2}}{n_z} \\ \phi_n &= \tan^{-1} \frac{n_y}{n_x} \end{aligned} \quad (23)$$

Figure 13A:
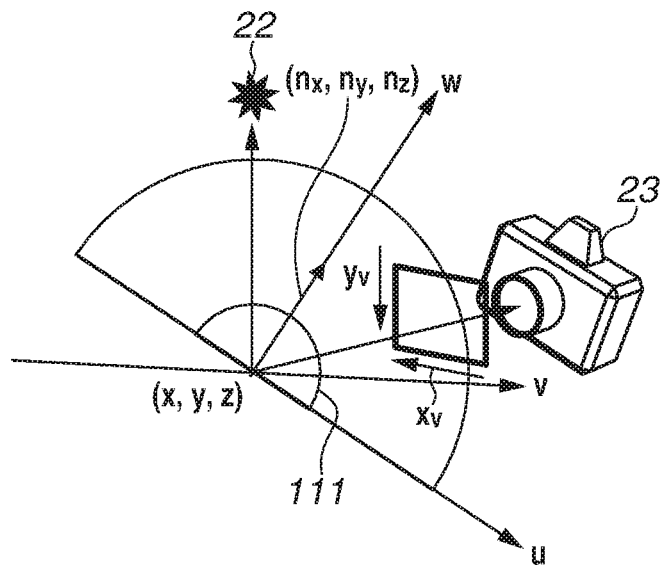
FIGS. 13A, 13B, and 13C are conceptual views illustrating a relation among a normal vector and a virtual environment map, and a shadowing map.
Figure 13B:
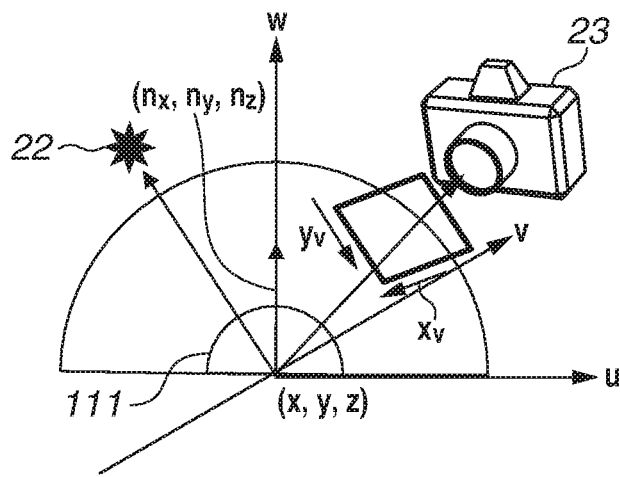

Reflection characteristics are defined by a coordinate system of which the normal vector coincides with the z-axis direction in the XYZ coordinate system. Therefore, the global coordinate system (or XYZ coordinate system) into the UVW coordinate system based on the normal vector is to be converted. The conversion from the XYZ coordinate system to the UVW coordinate system will be described below. FIG. 13A illustrates a relation between a normal vector and a hemispheric virtual environment map 111 in the global coordinate system. FIG. 13B illustrate a relation between a normal vector and the hemispheric virtual environment map 111 in the UVW coordinate system based on the normal vector.

Figure 13C:
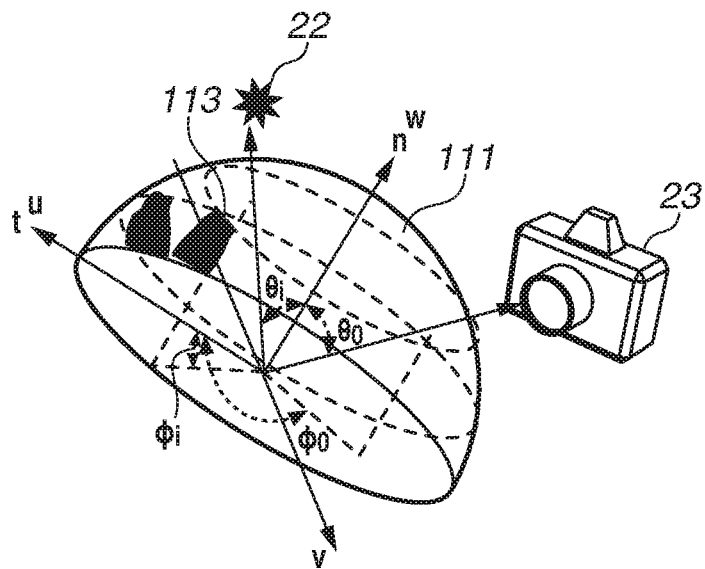

FIG. 13C illustrates a relation between the hemispheric virtual environment map 111 and a shadowing map in the global coordinate system. Even if the hemispheric virtual environment map 111 can be generated, light from all lighting directions in the virtual environment map 111 does not necessarily enters the point X on the three-dimensional real object 61. When incident light is intercepted by the self-shading 113, the reflection characteristics in consideration of shadowing is to be estimated.

Applying the visible functions $V(x, \omega_i)$ and $V(x, \omega_r)$ defined by the formula (22) to the rendering formula (2) gives the formula (24).

$$L_o(x, \omega_r) = V(x, \omega_r)\left\{L_e(x, \omega_r) + \int_\Omega L_i(x, \omega_i)V(x, \omega_i)f_r(x, \omega_i, \omega_r)\cos(\theta_i)d\omega_i\right\} \quad (24)$$

For simplicity, taking the real object 61 that does not emit spontaneous light, as an example gives the formula (25).

$$L_o(x, \omega_r) = V(x, \omega_r)\int_\Omega L_i(x, \omega_i)V(x, \omega_i)f_r(x, \omega_i, \omega_r)\cos(\theta_i)d\omega_i \quad (25)$$

When a method of discretizing the formula (25) to segmenting the light source patterns of direct light radiated from all directions and indirect light into m segmentation solid angles $\Delta\omega_j$ (j=1 to m) is applied to each of the $N_i$ light source patterns, the simultaneous linear formula (26) is given for the viewing direction $k \in [1, N_v]$. In this case, there is a relation represented by the formula (27) between the omni-directional solid angle $\Omega$ and the segmentation solid angles $\Delta\omega_j$ (j=1 to m).

$$\left.\begin{aligned}L_o(x, k, 1) &= V(x, k)\sum_{j=1}^{m} L_i(x, j, 1)V(x, j)f_r(x, j, k)\cos(\theta_j)\Delta\omega_j \\ L_o(x, k, 2) &= V(x, k)\sum_{j=1}^{m} L_i(x, j, 2)V(x, j)f_r(x, j, k)\cos(\theta_j)\Delta\omega_j \\ &\vdots \\ L_o(x, k, N_i) &= V(x, k)\sum_{j=1}^{m} L_i(x, j, N_i)V(x, j)f_r(x, j, k)\cos(\theta_j)\Delta\omega_j\end{aligned}\right\} \quad (26)$$

$$\sum_{j=1}^{m} \Delta\omega_j = \Omega \quad (27)$$

When the simultaneous linear formula (26) is to be expressed using a matrix, the formula (26) can be rearranged as the formula (28). When the formula (28) is solved for $f_r(x, 1, k)$ to $f_r(x, m, k)$ that are m BRDFs, the BRDFs for the m lighting directions (1 to m) and one viewing direction ($k \in [1, N_v]$) can be calculated by the formula (29).

$$\begin{pmatrix} L_o(x, k, 1) \\ L_o(x, k, 2) \\ \vdots \\ L_o(x, k, N_i) \end{pmatrix} = V(x, k)\begin{pmatrix} L_i(x, 1, 1) & L_i(x, 2, 1) & \cdots & L_i(x, m, 1) \\ L_i(x, 1, 2) & L_i(x, 2, 2) & \cdots & L_i(x, m, 2) \\ \vdots & \vdots & \vdots & \vdots \\ L_i(x, 1, N_i) & L_i(x, 2, N_i) & \cdots & L_i(x, m, N_i) \end{pmatrix} \quad (28)$$

$$\begin{pmatrix} V(x, 1)f_r(x, 1, k)\cos(\theta_1)\Delta\omega_1 \\ V(x, 2)f_r(x, 2, k)\cos(\theta_2)\Delta\omega_2 \\ \vdots \\ V(x, m)f_r(x, m, k)\cos(\theta_m)\Delta\omega_m \end{pmatrix}$$

$$= V(x, k)\begin{pmatrix} L_i(x, 1, 1)V(x, 1)\cos(\theta_1)\Delta\omega_1 & L_i(x, 2, 1)V(x, 2)\cos(\theta_2)\Delta\omega_2 & \cdots & L_i(x, m, 1)V(x, m)\cos(\theta_m)\Delta\omega_m \\ L_i(x, 1, 2)V(x, 1)\cos(\theta_1)\Delta\omega_1 & L_i(x, 2, 2)V(x, 2)\cos(\theta_2)\Delta\omega_2 & \cdots & L_i(x, m, 2)V(x, m)\cos(\theta_m)\Delta\omega_m \\ \vdots & \vdots & \vdots & \vdots \\ L_i(x, 1, N_i)V(x, 1)\cos(\theta_1)\Delta\omega_1 & L_i(x, 2, N_i)V(x, 2)\cos(\theta_2)\Delta\omega_2 & \cdots & L_i(x, m, N_i)V(x, m)\cos(\theta_m)\Delta\omega_m \end{pmatrix}\begin{pmatrix} f_r(x, 1, k) \\ f_r(x, 2, k) \\ \vdots \\ f_r(x, m, k) \end{pmatrix}$$

$$= V(x, k)(A)\begin{pmatrix} f_r(x, 1, k) \\ f_r(x, 2, k) \\ \vdots \\ f_r(x, m, k) \end{pmatrix}$$

$$\begin{pmatrix} f_r(x, 1, k) \\ f_r(x, 2, k) \\ \vdots \\ f_r(x, m, k) \end{pmatrix} = \frac{1}{V(x, k)} (A^{-1}) \begin{pmatrix} L_o(x, k, 1) \\ L_o(x, k, 2) \\ \vdots \\ L_o(x, k, N_i) \end{pmatrix} \quad (29)$$

$$= \frac{1}{V(x,k)} \begin{pmatrix} \frac{L_i(x,1,1)V(x,1)}{\cos(\theta_1)\Delta\omega_1} & \frac{L_i(x,2,1)V(x,2)}{\cos(\theta_2)\Delta\omega_2} & \cdots & \frac{L_i(x,m,1)V(x,m)}{\cos(\theta_m)\Delta\omega_m} \\ \frac{L_i(x,1,2)V(x,1)}{\cos(\theta_1)\Delta\omega_1} & \frac{L_i(x,2,2)V(x,2)}{\cos(\theta_2)\Delta\omega_2} & \cdots & \frac{L_i(x,m,2)V(x,m)}{\cos(\theta_m)\Delta\omega_m} \\ \vdots & \vdots & \vdots & \vdots \\ \frac{L_i(x,1,N_i)V(x,1)}{\cos(\theta_1)\Delta\omega_1} & \frac{L_i(x,2,N_i)V(x,2)}{\cos(\theta_2)\Delta\omega_2} & \cdots & \frac{L_i(x,m,N_i)V(x,m)}{\cos(\theta_m)\Delta\omega_m} \end{pmatrix}^{-1}$$

$$\begin{pmatrix} L_o(x, k, 1) \\ L_o(x, k, 2) \\ \vdots \\ L_o(x, k, N_i) \end{pmatrix}$$

However, with regard to the viewing direction (k ∈[1, $N_v$]) with V(x, k)=0, the point X on the three-dimensional real object 61 cannot be imaged from the viewing direction because of self-shadowing, and therefore the BRDF cannot be obtained. Further, when the lighting direction (j ∈[1, m]) has V(x, j)=0 because of self-shading, column elements of the matrix A represented by the formula (28) become 0, and therefore the BRDF for the lighting direction (j ∈[1, m]) with V(x, j)=0 cannot be obtained.

More specifically, when self-shadowing or self-shading exists, information about the shadowed portion is missing, and therefore not all BRDFs (m*$N_v$) for the m lighting directions and the $N_v$ viewing directions can be obtained.

On the other hand, the estimation of reflection characteristics in consideration of shadowing enables not only improvement of the estimation accuracy but also shortening of the processing time compared to the estimation of reflection characteristics without consideration of shadowing. As illustrated in FIG. 13C, the hemispheric virtual environment map 111 includes the self-shading 113 due to the ear portions of the rabbit.

Figure 14A:
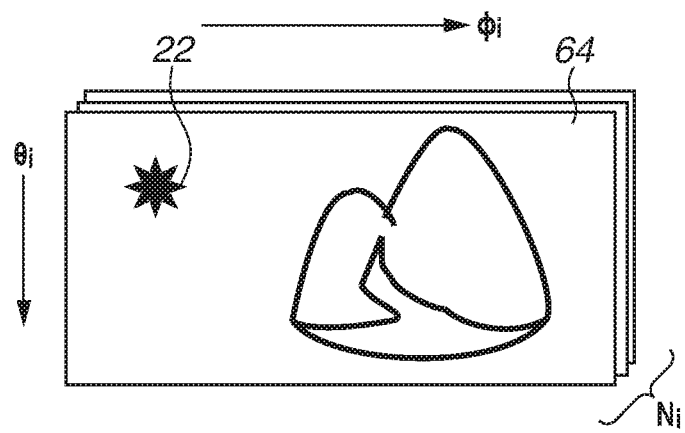
FIGS. 14A, 14B, and 14C are conceptual views illustrating virtual environment maps and virtual line-of-sight maps in consideration of a shadowing map.
Figure 14B:
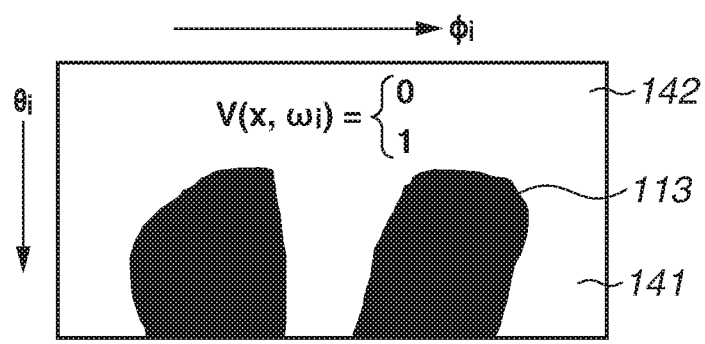
Figure 14C:
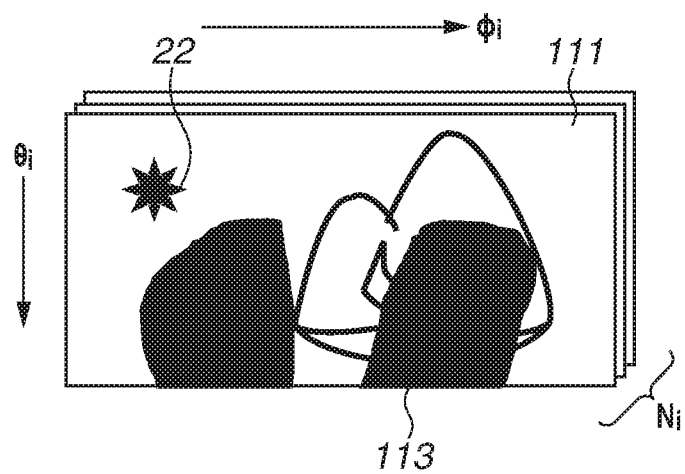

FIGS. 14A, 14B, and 14C are conceptual views illustrating the virtual environment map 111 in consideration of a shadowing map. There are two different methods of generating the virtual environment map 111 in consideration of a shadowing map: one method applies the shadowing map 142 as a mask to the virtual environment map information 64 without consideration of a shadowing map, and the other method performs successive processing based on the visible region 141 of the shadowing map 142. When generating the hemispheric virtual environment map 111, successive processing based on the visible region 141 of the shadowing map 142 enables omission of such processing as corresponding point search (determining the pixel values of corresponding points on the virtual environment map 111 based on a plurality of environment maps) for the shadowed portion 113.

In step S28, the CPU 1 performs virtual line-of-sight map generation processing to generate a virtual line-of-sight map for the point X on the three-dimensional real object 61 based on the BTF images acquired by the captured image information acquisition processing (step S23). A virtual line-of-sight map represents the radiation luminance (or luminance) $L_o$ in the $N_v$ viewing directions for the point X on the three-dimensional real object 61.

Figure 15:
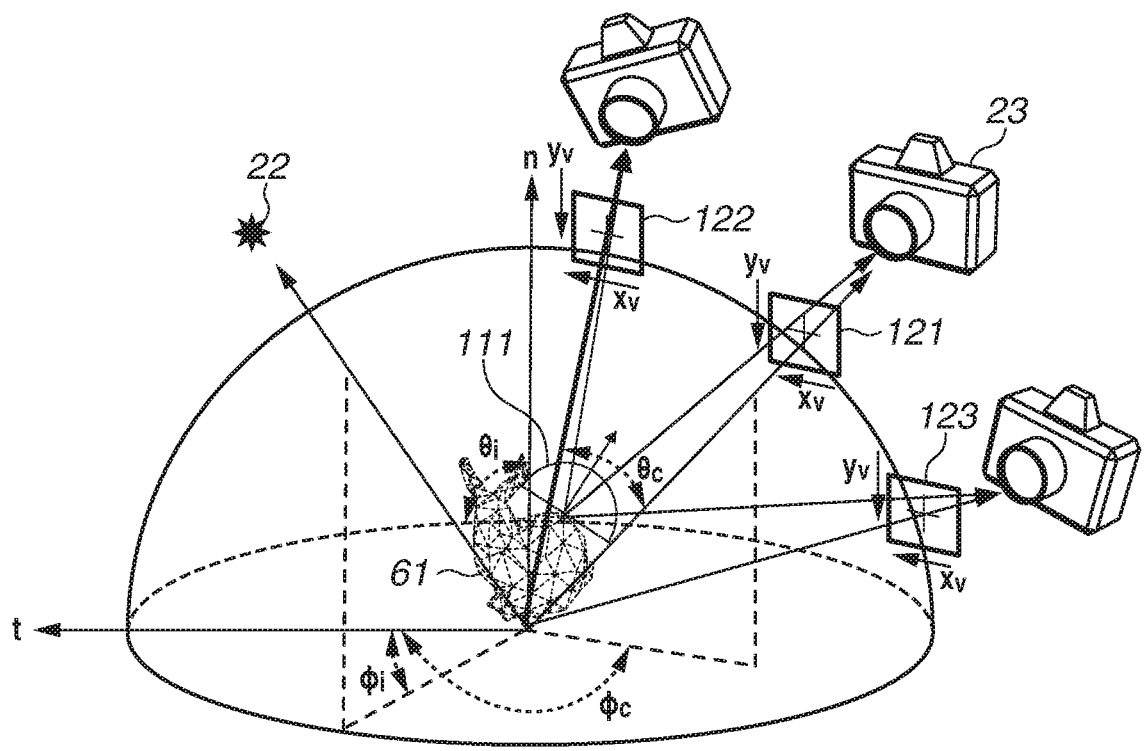
FIG. 15 illustrates an example of generating a virtual line-of-sight map.
Figure 16A:
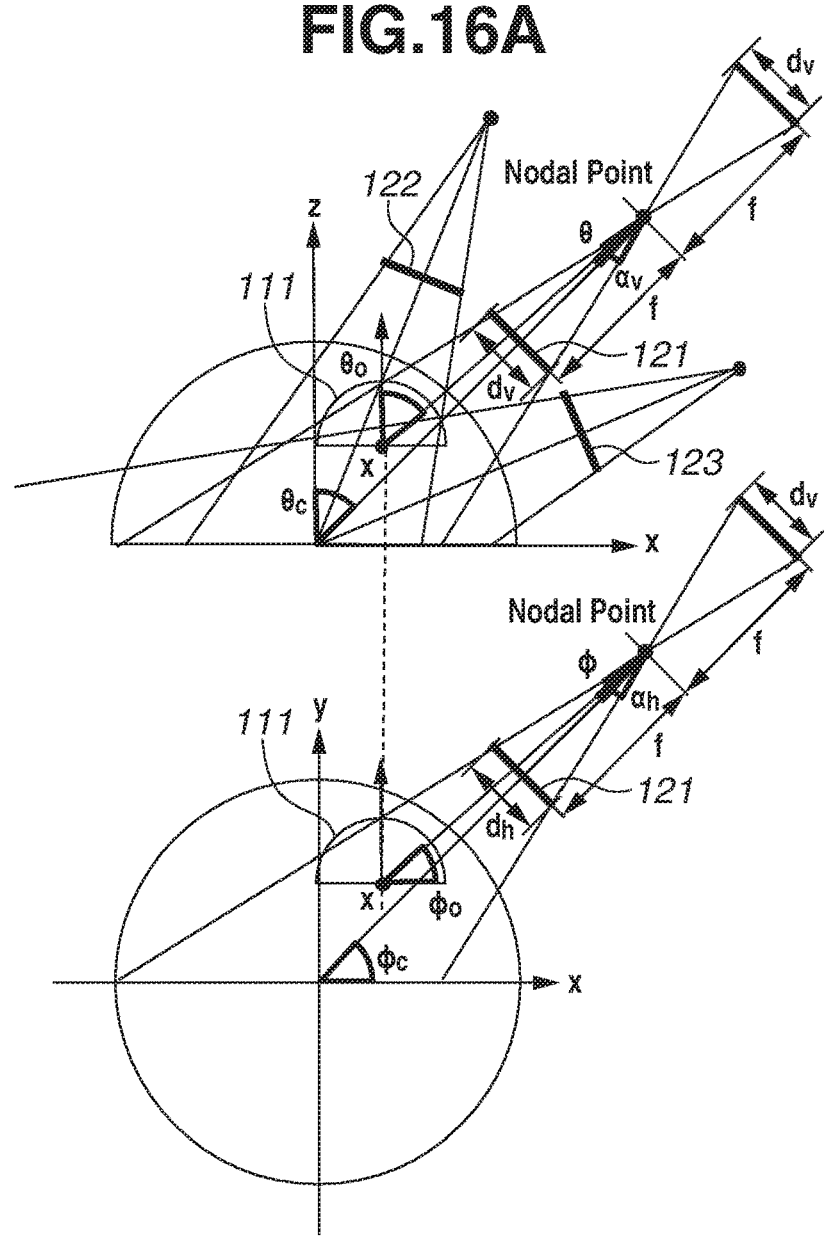
FIGS. 16A and 16B illustrate an example of generating a virtual line-of-sight map.
Figure 16B:
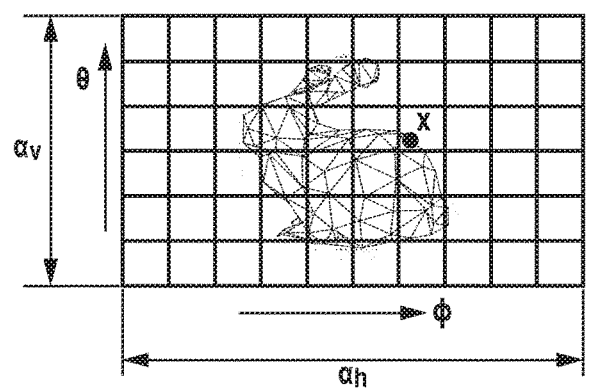

FIGS. 15, 16A, and 16B illustrate an example of generating a virtual line-of-sight map according to the second exemplary embodiment.

FIG. 15 illustrates the captured image information acquisition processing (step S23) in which the CPU 1 performs, by using $N_v$ digital cameras 23, HDR imaging on the three-dimensional real object 61 irradiated with the light source 22 to acquire BTF images (captured images) 121 to 123. As described above, the optical axis of each of the $N_v$ digital cameras 23 coincides with the origin of the global coordinate system for the stage on which the three-dimensional real object 61 is placed. Therefore, the center pixel of each of the captured images 121 to 123 is represented by the viewing direction ($\theta_c$, $\varphi_c$) for the origin of the global coordinate system.

The viewing directions ($\theta_o$, $\varphi_o$) for all of the points X on the three-dimensional real object 61 are not identical to the viewing directions ($\theta_c$, $\varphi_c$) of each digital camera 23 for the origin of the global coordinate system. More specifically, the magnitude of an error from the viewing direction ($\theta_c$, $\varphi_c$) increases as size of the real object 61 increases relative to the distance from the origin of the global coordinate system to the digital camera 23. FIG. 16A illustrates a relation between the viewing direction ($\theta_c$, $\varphi_c$) for the origin of the global coordinate system (or XYZ coordinate system) and the viewing direction for the point X on the three-dimensional real object 61 ($\theta_o$, $\varphi_o$) for the captured image 121. The top of FIG. 16A is a front view illustrating the XZ plane, and the bottom of FIG. 16A is a top view illustrating the XY plane. According to the present exemplary embodiment, a pinhole camera model is used for simplicity. Referring to the front view, the formula (30) is given, where $\alpha_v$ denotes the vertical viewing angle, $d_v$ denotes the vertical width of an image sensor, and f denotes the focal length.

$$\tan\frac{\alpha_v}{2} = \frac{d_v}{2f} \quad (30)$$

When the formula (30) is rearranged, the vertical viewing angle $\alpha_v$ can be represented by the formula (31).

$$\alpha_v = 2\tan^{-1}\frac{d_v}{2f} \quad (31)$$

Likewise, referring to the top view, the formula (32) is given, where $\alpha_h$ denotes the horizontal viewing angle, $d_h$ denotes the horizontal width of the image sensor, and f denotes the focal length.

$$\tan\frac{\alpha_h}{2} = \frac{d_h}{2f} \quad (32)$$

When the formula (32) is rearranged, the horizontal viewing angle $\alpha_h$ can be represented by the formula (33).

$$\alpha_h = 2\tan^{-1}\frac{d_h}{2f} \quad (33)$$

Based on the formulas (31) and (33), the vertical viewing angle $\alpha_v$ and the horizontal viewing angle $\alpha_h$ can be calculated based on the size of the image sensor (the vertical width $d_v$ and the horizontal width $d_h$) and the focal length f.

FIG. 16B illustrates a captured image of the digital camera 23 captured with the vertical viewing angle $\alpha_v$ and the horizontal viewing angle $\alpha_h$. The vertical viewing angle $\alpha_v$ and the horizontal viewing angle $\alpha_h$ correspond to the height and the width of the captured image, respectively. The point X on the three-dimensional real object 61 corresponds to the coordinates $(\theta, \varphi)$ on the captured image. The viewing direction $(\theta_o, \varphi_o)$ for the point X on the three-dimensional real object 61 can be represented by the formulas (34) and (35) using the viewing direction $(\theta_c, \varphi_c)$ for the origin and the coordinates $(\theta, \varphi)$ on the captured image in the global coordinate system (or XYZ coordinate system).

$$\left.\begin{array}{l}\theta_o = \theta_c + \theta \\ -\frac{\alpha_v}{2} \leq \theta \leq \frac{\alpha_v}{2}\end{array}\right\} \quad (34)$$

$$\left.\begin{array}{l}\phi_o = \phi_c - \phi \\ -\frac{\alpha_h}{2} \leq \phi \leq \frac{\alpha_h}{2}\end{array}\right\} \quad (35)$$

In this case, when the coordinates $(\theta, \varphi)$ on the captured image are equal to the coordinates of the center pixel $(0, 0)$, the viewing direction $(\theta_o, \varphi_o)$ refers to the viewing direction $(\theta_c, \varphi_c)$ for the origin of the global coordinate system, as described above.

More specifically, in the BTF images 121 to 123 captured by the $N_v$ digital cameras 23, the CPU 1 perform corresponding point search on the point X on the three-dimensional real object 61 to identify the coordinates $(\theta, \varphi)$ on each captured image. Further, when the formulas (34) and (35) are applied to the identified coordinates $(\theta, \varphi)$ on each captured image, the CPU 1 can generate a virtual line-of-sight map for the point X on the three-dimensional real object 61.

A virtual line-of-sight map represents the radiation luminance (or luminance) $L_o$ in the $N_v$ viewing directions for the point X on the three-dimensional real object 61. When the three-dimensional real object 61 is irradiated with the $N_i$ light source patterns, the number of virtual line-of-sight maps for the point X on the three-dimensional real object 61 is given by $N_i * N_v$. Known techniques such as Scale-Invariant Feature Transform (SIFT) can be used for corresponding point search.

A virtual line-of-sight map may be formed by plotting the radiation luminance (or luminance) $L_o$ on respective line-of-sight coordinates on the omnidirectional image or by storing the radiation luminance (or luminance) $L_o$ for respective viewing directions in list form. When generating a virtual line-of-sight map, taking a shadowing map into consideration enables detecting in advance the viewing direction subjected to self-shadowing, making it possible to shorten the processing time.

Figure 17A:
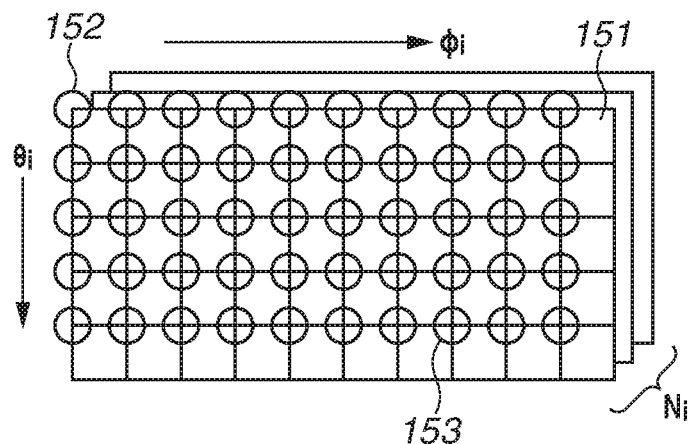
FIGS. 17A, 17B, and 17C are conceptual views illustrating virtual environment maps and virtual line-of-sight maps in consideration of a shadowing map.
Figure 17B:
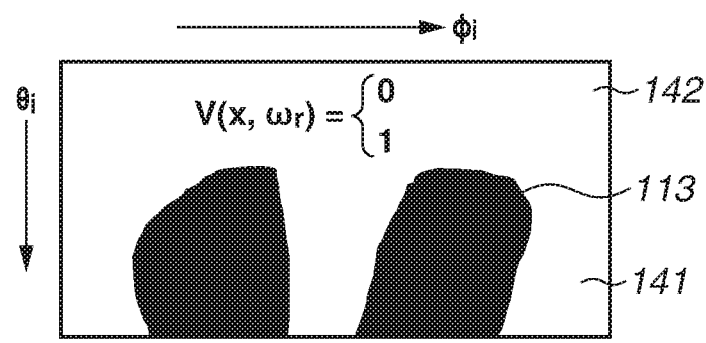
Figure 17C:
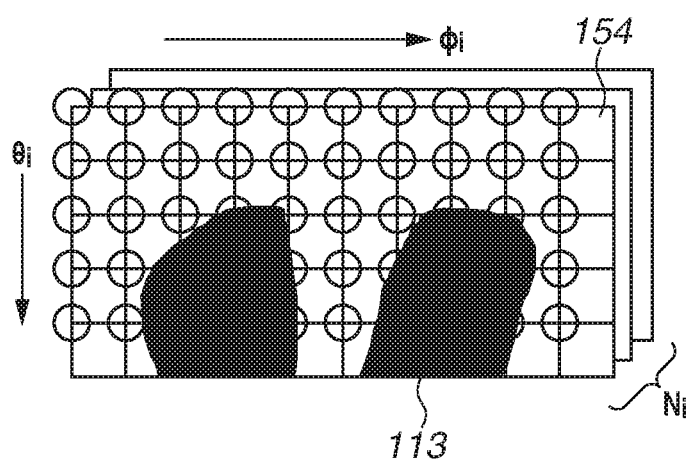

FIGS. 17A, 17B, and 17C are conceptual views illustrating a virtual line-of-sight map 154 in consideration of a shadowing map. There are two different methods of generating the virtual environment map 154 in consideration of a shadowing map: one method applies the shadowing map 142 as a mask to a virtual line-of-sight map 151 without consideration of a shadowing map, and the other method performs successive processing based on the visible region 141 of the shadowing map 142. When generating the hemispheric virtual environment map 154, successive processing based on the visible region 141 of the shadowing map 142 enables omission of such processing as corresponding point search (determining the pixel values of corresponding points based on captured images) for the shadowed portions 113.

In step S29, the CPU 1 performs coordinate conversion processing to convert the virtual environment map and the virtual line-of-sight map for the point X on the three-dimensional real object 61 from the global coordinate system (or XYZ coordinate system) into the UVW coordinate system. More specifically, the CPU 1 converts the virtual environment map (lighting direction) and the virtual line-of-sight map (viewing direction) for the point X on the three-dimensional real object 61 defined in the global coordinate system into those in the UVW coordinate system based on the normal vector $(n_x, n_y, n_z)$ for the point X on the three-dimensional real object 61.

Reflection characteristics are defined such that the direction of the normal vector coincides with the z-axis direction in the XYZ coordinate system. Therefore, the CPU 1 defines the UVW coordinate system such that the direction of the normal vector for the point X on the three-dimensional real object 61 coincides with the w axis.

Figure 18:
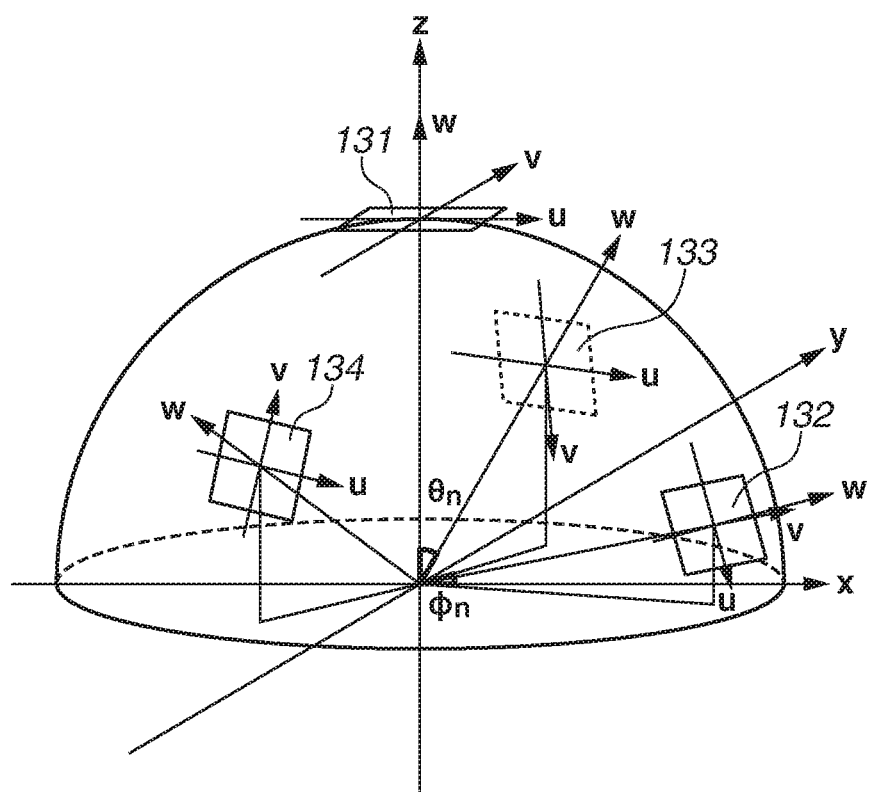
FIG. 18 illustrates a relation between the global coordinate system and the UVW coordinate system.

FIG. 18 illustrates a relation between the global coordinate system (or XYZ coordinate system) and the UVW coordinate system. The direction of the w axis of the UVW coordinate system coincides with the direction of the normal vector for the point X on the three-dimensional real object 61, and therefore can be uniquely determined. On the other hand, the directions of the u and v axes are not defined based on the reflection characteristics, and therefore cannot be uniquely determined.

According to the present exemplary embodiment, the UVW coordinate system is defined such that the directions of the u and v axes of the UVW coordinate system continuously change according to the direction of the normal vector (w axis).

If the direction of the normal vector (w axis) coincides with the direction of the z axis, as illustrated in FIG. 18, the directions of the u and v axes in a tangent plane 131 are considered to coincide with the directions of the x and y axes, respectively. The directions of the u and v axes in the tangent plane 132 when the normal vector is rotated around the y axis are considered to coincide with the directions thereof when the tangent plane 131 is rotated around the y axis. The directions of the u and v axes in the tangent planes 133 and 134 when the normal vector is rotated around the x axis are considered to coincide with the directions thereof when the tangent plane 131 is rotated around the x axis.

The virtual environment map and the virtual line-of-sight map for the point X on the real object 61 defined in the global coordinate system (or XYZ coordinate system) is represented by the spherical coordinates. Therefore, when the spherical coordinates (r, θ, φ) in the XYZ coordinate system are represented by the orthogonal coordinates (x, y, z), the formula (36) is given.

$$\begin{pmatrix} x \\ y \\ z \end{pmatrix} = \begin{pmatrix} r\sin\theta\cos\phi \\ r\sin\theta\sin\phi \\ r\cos\theta \end{pmatrix} \tag{36}$$

Likewise, when the spherical coordinates (r', θ', φ') in the UVW coordinate system are represented by the orthogonal coordinates (u, v, w), the formula (37) is given.

$$\begin{pmatrix} u \\ v \\ w \end{pmatrix} = \begin{pmatrix} r'\sin\theta'\cos\phi' \\ r'\sin\theta'\sin\phi' \\ r'\cos\theta' \end{pmatrix} \tag{37}$$

When the orthogonal coordinates (u, v, w) in the UVW coordinate system are represented by the spherical coordinates (r', θ', φ'), the formula (38) is given.

$$\left. \begin{aligned} r' &= \sqrt{u^2 + v^2 + w^2} \\ \phi' &= \tan^{-1}\frac{v}{u} \\ \theta' &= \tan^{-1}\frac{\sqrt{u^2+v^2}}{w} \end{aligned} \right\} \tag{38}$$

The CPU 1 converts the virtual environment map (lighting direction) and the virtual line-of-sight map (viewing direction) for the point X on the three-dimensional real object 61 defined in the global coordinate system into those in the UVW coordinate system based on the normal vector ($n_x$, $n_y$, $n_z$) for the point X on the three-dimensional real object 61. To this end, the CPU 1 applies the formula (39) that is a three-dimensional rotation matrix for converting the XYZ coordinate system into the UVW coordinate system, by using the formula (23) to obtain the polar angle θn and the azimuth angle φn of the normal vector ($n_x$, $n_y$, $n_z$). The XYZ coordinate system may be used instead of the global coordinate system.

$$\begin{pmatrix} u \\ v \\ w \end{pmatrix} = R_z(\phi_n)R_y(-\theta_n)R_z(-\phi_n)\begin{pmatrix} x \\ y \\ z \end{pmatrix} \tag{39}$$

$$= \begin{pmatrix} \cos(\phi_n) & -\sin(\phi_n) & 0 \\ \sin(\phi_n) & \cos(\phi_n) & 0 \\ 0 & 0 & 1 \end{pmatrix}\begin{pmatrix} \cos(-\theta_n) & 0 & \sin(-\theta_n) \\ 0 & 1 & 0 \\ -\sin(-\theta_n) & 0 & \cos(-\theta_n) \end{pmatrix}$$

$$\begin{pmatrix} \cos(-\phi_n) & -\sin(-\phi_n) & 0 \\ \sin(-\phi_n) & \cos(-\phi_n) & 0 \\ 0 & 0 & 1 \end{pmatrix}\begin{pmatrix} x \\ y \\ z \end{pmatrix}$$

$$= \begin{pmatrix} \cos\phi_n & -\sin\phi_n & 0 \\ \sin\phi_n & \cos\phi_n & 0 \\ 0 & 0 & 1 \end{pmatrix}\begin{pmatrix} \cos\theta_n & 0 & -\sin\theta_n \\ 0 & 1 & 0 \\ \sin\theta_n & 0 & \cos\theta_n \end{pmatrix}$$

$$\begin{pmatrix} \cos\phi_n & \sin\phi_n & 0 \\ -\sin\phi_n & \cos\phi_n & 0 \\ 0 & 0 & 1 \end{pmatrix}\begin{pmatrix} x \\ y \\ z \end{pmatrix}$$

$$= \begin{pmatrix} \cos\phi_n & -\sin\phi_n & 0 \\ \sin\phi_n & \cos\phi_n & 0 \\ 0 & 0 & 1 \end{pmatrix}$$

$$\begin{pmatrix} \cos\theta_n\cos\phi_n & \cos\theta_n\sin\phi_n & -\sin\theta_n \\ -\sin\phi_n & \cos\phi_n & 0 \\ \sin\theta_n\cos\phi_n & \sin\theta_n\sin\phi_n & \cos\theta_n \end{pmatrix}\begin{pmatrix} x \\ y \\ z \end{pmatrix}$$

$$= \begin{pmatrix} \cos\theta_n\cos^2\phi_n + \sin^2\phi_n & \sin\phi_n\cos\phi_n(\cos\theta_n-1) & -\sin\theta_n\cos\phi_n \\ \sin\phi_n\cos\phi_n(\cos\theta_n-1) & \cos\theta_n\sin^2\phi_n+\cos^2\phi_n & -\sin\theta_n\sin\phi_n \\ \sin\theta_n\cos\phi_n & \sin\theta_n\sin\phi_n & \cos\phi_n \end{pmatrix}\begin{pmatrix} x \\ y \\ z \end{pmatrix}$$

Here, Rz denotes a rotation matrix expressing the rotation around the z axis, and Ry denotes a rotation matrix expressing the rotation around the y axis. The rotational direction of Rz is such that the x axis is moved toward the y axis, and the rotational direction of Ry is such that the z axis is moved toward the x axis.

The CPU 1 applies the formulas (36), (39), and (38) for each lighting direction ($\theta_i$, $\varphi_i$) of the virtual environment map for the point X on the three-dimensional real object 61 defined in the global coordinate system (or XYZ coordinate system). Then, the CPU 1 converts the virtual environment map in the global coordinate system into a virtual environment map in the UVW coordinate system based on the normal vector ($n_x$, $n_y$, $n_z$) for the point X on the three-dimensional real object 61.

Likewise, the CPU 1 applies the formulas (36), (39), and (38) for each viewing direction ($\theta_o$, $\varphi_o$) of the virtual line-of-sight map for the point X on the three-dimensional real object 61 defined in the global coordinate system (or XYZ coordinate system). Then, the CPU 1 converts the virtual line-of-sight map in the global coordinate system into a virtual line-of-sight map in the UVW coordinate system based on the normal vector ($n_x$, $n_y$, $n_z$) for the point X on the three-dimensional real object 61.

In the UVW coordinate system for the point X on the three-dimensional real object 61, the above-described processing can provide a relation between the environment map information and the captured image information that is the same as the relation therebetween according to the first exemplary embodiment. Therefore, the CPU 1 is to perform processing equivalent to the processing according to the first exemplary embodiment on the point X on the three-dimensional real object 61 to estimate the reflection characteristics at the point X on the three-dimensional real object 61.

More specifically, in step S30, the CPU 1 first performs light source matrix generation processing to generate a light source matrix ($N_i$*m) determined based on the number of light source patterns ($N_i$) for the environment map information and the number of segmentation solid angles (m) obtained by segmenting the environment map information.

Figure 19:
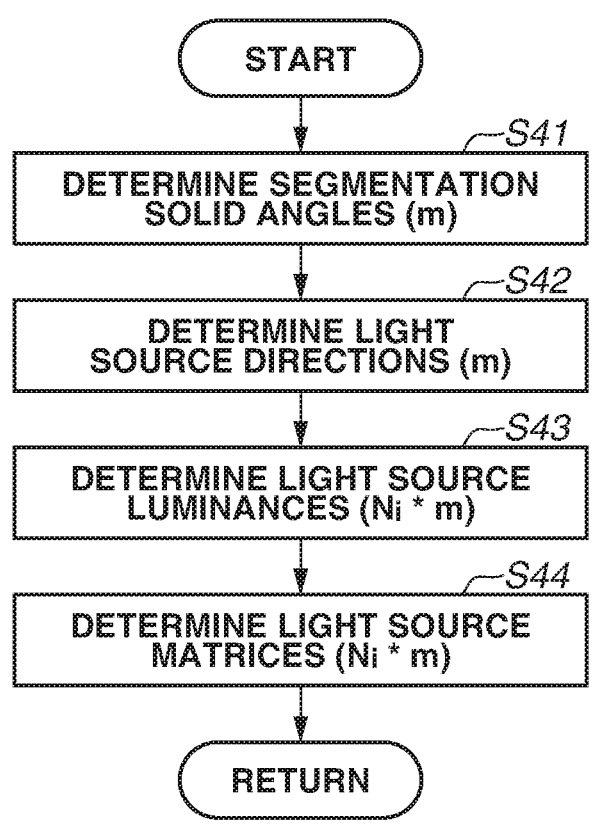
FIG. 19 is a flowchart illustrating estimation processing of reflection characteristics of a three-dimensional real object.

FIG. 19 is a flowchart illustrating in detail the light source matrix generation processing (step S30) according to the second exemplary embodiment. In the light source matrix generation processing (step S30), the CPU 1 performs the processing (steps S41, S42, S43, and S44) identical to the segmentation solid angle determination processing (step S3), the lighting direction determination processing (step S4), the light source luminance determination processing (step S5), and the light source matrix determination processing (step S6) according to the first exemplary embodiment. More specifically, the CPU 1 segments each virtual environment map in the UVW coordinate system for the $N_i$ light source patterns into m segmentation solid angles, and determines a light source matrix ($N_i$*m) for the point X on the three-dimensional real object 61.

In step S31, the CPU 1 performs reflection characteristic estimation processing to estimate the reflection characteristics for the point X on the three-dimensional real object 61. The CPU 1 estimates the reflection characteristics by applying to the formula (7) or (29) the light source matrix ($N_i$*m) for the point X on the real object 61 and the radiation luminance (or luminance) $L_o$ (1 to $N_i$) in the $N_v$ viewing directions for the point X on the real object 61 obtained from the virtual line-of-sight map in the UVW coordinate system.

In step S32, the CPU 1 performs reflection model parameter estimation processing to apply fitting to the discrete reflection characteristics for the point X on the three-dimensional real object 61 by using parameters of a reflection model. In step S33, the CPU 1 determines whether the processing in steps S25 to S32 is completed for all of the points X set on the three-dimensional real object 61. When the processing is not completed (NO in step S33), the CPU 1 virtually moves the point X on the three-dimensional real object 61 and performs the processing from step S25. On the other hand, when the processing is completed (YES in step S33), the CPU 1 ends the processing illustrated in FIG. 10.

Effects of Second Exemplary Embodiment

As described above, according to the present exemplary embodiment, a virtual environment map and a virtual line-of-sight map are generated at each point on a three-dimensional real object. This enables estimation of the reflection characteristics on the three-dimensional real object at a high speed with a high accuracy with the real object, light sources, and digital cameras remained fixed.

Further, according to the present exemplary embodiment, the UVW coordinate system based on a normal vector is defined at each point set on the three-dimensional real object, and the reflection characteristics are described based on the coordinate system of concern. More specifically, a coordinate system based on the normal vector is defined at each point set on the real object, and the reflection characteristics are described based on the coordinate system of concern. This enables unique description of the reflection characteristics at each point on the three-dimensional real object.

A third exemplary embodiment will be described below. The second exemplary embodiment has been described above centering on a method of virtually moving a measurement point X in consideration of the shadowing map 142 when estimating the reflection characteristics at the point X on the three-dimensional real object 61. In the reflection characteristic estimation in consideration of the shadowing map 142, the processing speed can be improved by skipping the processing for the shadowed portion 113. However, there arises a situation that, of combinations of the BRDFs (m*$N_v$) for the m lighting directions and the $N_v$ viewing directions, the BRDF for the shadowed portion cannot be estimated because of a lack of information.

The present exemplary embodiment will be described below centering on a method of complementing a lack of information due to shadowing while restraining the BRDF estimation accuracy degradation due to shadowing in consideration of the shadowing map 142.

The following briefly describes the present exemplary embodiment centering on differences from the first and second exemplary embodiments. Elements identical to those in the first and second exemplary embodiments will be omitted.

(Restraining BRDF Estimation Accuracy Degradation Due to Shadowing)

Figure 20A:
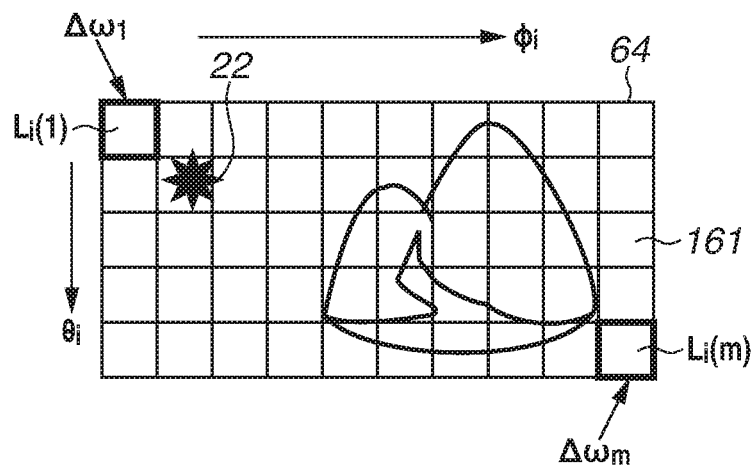
FIGS. 20A, 20B, and 20C illustrates examples of methods of determining segmentation solid angles in consideration of shadowing.
Figure 20B:
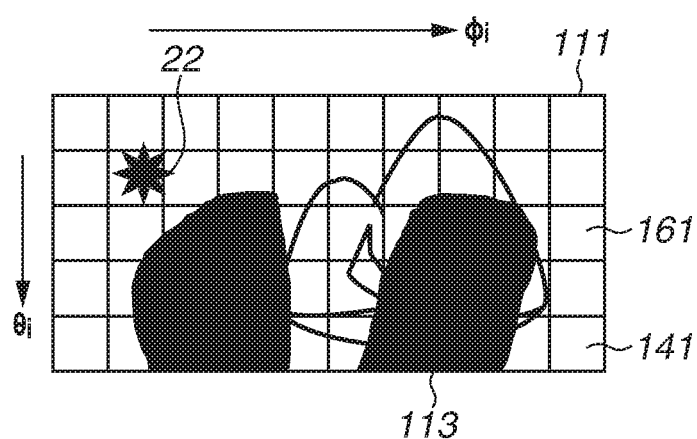
Figure 20C:
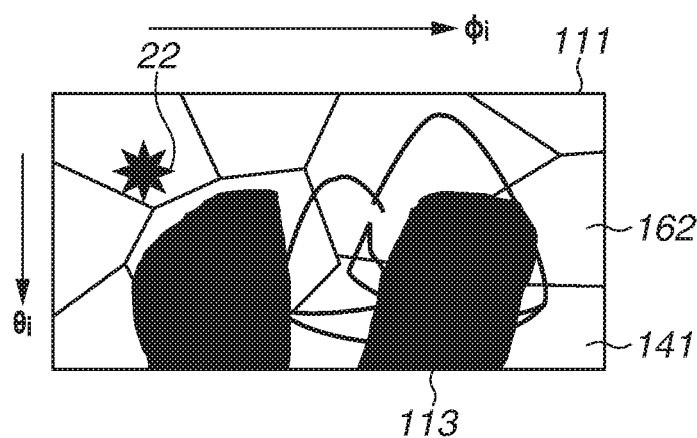

FIGS. 20A, 20B, and 20C illustrate a method of determining segmentation solid angles in consideration of shadowing according to the third exemplary embodiment.

FIG. 20A illustrates an example of determining segmentation solid angles 161 by using the virtual environment map information 64 with a viewpoint set to the position of the point X on the three-dimensional real object 61, instead of the environment map information 41 illustrated in FIG. 4B.

FIG. 20B illustrates an example of applying the determined segmentation solid angles 161 illustrated in FIG. 20A to the virtual environment map 111 in consideration of shadowing according to the formulas (26) and (27). Since the segmentation solid angles 161 are determined based on the virtual environment map information 64 without consideration of shadowing, the shadowed portion 113 and the unshadowed portion 141 may coexist in the segmentation solid angles 161.

As described above in the lighting direction determination processing (step S4) according to the first exemplary embodiment, there are two different methods of determining the lighting direction ($\theta_j$, $\varphi_j$) of each segmentation solid angle $\Delta\omega_j$ (j=1 to m): one method uses the area center (gravity center), and the other method uses the luminance gravity center. In the above-described case where a shadowed portion and an unshadowed portion coexist, the method of using the luminance gravity center makes it possible to estimate the BRDF with a higher accuracy. This is because the method of using the area center (gravity center) determines the lighting direction regardless of shadowing, whereas the method of using the luminance gravity center determines the lighting direction in consideration of the radiation luminance (or luminance) $L_i$ of each pixel in the segmentation solid angles 161. However, the segmentation solid angles 161 determined regardless of shadowing are uniformly distributed over the hemisphere of the virtual environment map 111 in consideration of shadowing. On the other hand, the coexistence rate of the shadowed portion 113 and the unshadowed portion 141 in the segmentation solid angles 161 becomes uneven. Accordingly, the distribution of light directions determined from the segmentation solid angles 161 where a shadowed portion and an unshadowed portion coexist also becomes nonuniform, degrading the BRDF estimation accuracy.

FIG. 20C illustrates an example of determining segmentation solid angles 162 by using only the unshadowed portion 141 of the virtual environment map 111 in consideration of shadowing to prevent nonuniformity of the distribution of light directions determined from the segmentation solid angles 161 where a shadowed and an unshadowed portion coexist. For example, region segmentation with a Voronoi diagram on the unshadowed portion 141 is performed by using a method similar to the method illustrated in FIGS. 6A, 6B, and 6C, and to use a segmented region as the segmentation solid angles 162. The segmentation solid angles 162 segmented by using the Voronoi diagram include only segmentation solid angles where a shadowed portion and an unshadowed portion do not coexist, restraining the BRDF estimation accuracy degradation due to the coexistence of a shadowed portion and an unshadowed portion. More specifically, the present exemplary embodiment estimates the reflection characteristics of a real object by segmenting the environment maps into segmentation solid angles based on information indicating a visible region.

(Complementing Lack of Information Due to Shadowing)

As described above, in the reflection characteristic estimation in consideration of the shadowing map 142 according to the second exemplary embodiment (FIG. 10), the discrete reflection characteristics for the point X on the three-dimensional real object 61 can be acquired by the reflection characteristic estimation processing (step S31). However, of combinations of the BRDFs (m*$N_v$) for the m lighting directions and the $N_v$ viewing directions, the BRDF for the shadowed portion cannot be estimated.

Therefore, in the reflection model parameter estimation processing (step S32), the second exemplary embodiment applies reflection model fitting to an incomplete BRDF including a lack of information due to shadowing. As a result, the estimated parameters of the reflection model will include a large error in a portion with a lack of information due to shadowing.

FIG. 21 is a flowchart illustrating estimation processing of reflection characteristics of a three-dimensional real object in consideration of shadowing according to the third exemplary embodiment. The following briefly describes the present exemplary embodiment centering on differences from the first and second exemplary embodiments. Processing identical to that according to the first and second exemplary embodiments is assigned the same reference numerals, and redundant descriptions thereof will be omitted.

The CPU 1 acquires the discrete reflection characteristics for the point X on the three-dimensional real object 61 in the processing up to the reflection characteristic estimation processing (step S31). In this case, the discrete reflection characteristics mean an incomplete BRDF including a lack of information due to shadowing. The reflection model parameter estimation processing (step S32) is performed after the processing in step S33 and BRDF complement processing in steps S51 and S52 (described below).

In step S51, when the discrete reflection characteristics are obtained at all of the points X on the three-dimensional real object 61 in the determination processing (step S33), the CPU 1 determines whether the discrete reflection characteristics for each point X mean an incomplete BRDF. The CPU 1 can determine whether the discrete reflection characteristics at each point X mean an incomplete BRDF when applying the formula (29) in the reflection characteristic estimation processing (step S31).

More specifically, the CPU 1 can make the determination based on whether the lighting direction (j ∈ [1, m]) with V(x, j)=0 or the viewing direction (k∈[1, $N_v$]) with V(x, k)=0 exists. For example, in the reflection characteristic estimation processing (step S31), there is a case where the lighting direction (j ∈[1, m]) with V(x, j)=0 or the viewing direction (k∈[1, $N_v$]) with V(x, k)=0 exists. In such a case, presetting a flag for each point X enables simply performing the incomplete BRDF determination processing (step S51) at a high speed.

Then, the CPU 1 complements a lack of information due to an incomplete BRDF in the incomplete BRDF complement processing (step S52). Generally, in many cases, an adjacent portion of the point X on the three-dimensional real object 61 is made of the same material as the point X. Since the BRDF is a function reflecting only the surface material, the BRDF can be considered to be disassociated from surface unevenness. All of the BRDFs estimated in the reflection characteristic estimation processing (step S31) are represented in the UVW coordinate system converted by the coordinate conversion (step S29) such that the direction of the surface normal vector coincides with the w axis. Therefore, when the reflection characteristics mean isotropic reflection, the BRDF for the point X on the three-dimensional real object 61 and the BRDF for an adjacent point can be directly compared in the UVW coordinate system. On the other hand, when the reflection characteristics mean anisometric reflection, the BRDF for the point X on the three-dimensional real object 61 and the BRDF for an adjacent point can be directly compared by rotating the BRDFs around the w axis.

When the point X on the three-dimensional real object 61 and an adjacent point are made of the same material, the BRDFs for the two points will be identical. If an incomplete BRDF for the point X on the three-dimensional real object 61 partly coincides or highly correlates with the BRDF for an adjacent point, the two points are highly likely to be made of the same material. Therefore, the CPU 1 complements a portion with a lack of information due to shadowing by an incomplete BRDF for the point X on the three-dimensional real object 61, with the value of the BRDF for an adjacent point. More specifically, if information about reflection characteristics of the real object lacks due to shadowing, the CPU 1 complements the portion of concern with similar reflection characteristics at a peripheral portion.

Effects of Third Exemplary Embodiment

As described above, according to the present exemplary embodiment, the BRDF estimation accuracy degradation due to shadowing can be restrained by determining segmentation solid angles by using only an unshadowed portion in the virtual environment map.

Further, according to the present exemplary embodiment, a lack of information due to shadowing can be complemented with similar reflection characteristics at a peripheral portion. Thus, BRDF estimation accuracy degradation due to shadowing can be restrained.

According to the present exemplary embodiment, it is possible to improve the estimation accuracy of reflection characteristics of a real object without providing restrictions in a measurement environment.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2017-034504, filed Feb. 27, 2017, which is hereby incorporated by reference herein in its entirety.

What is claimed is:

1. An apparatus comprising:
   one or more processors; and
   one or more memories storing instructions, when executed by the one or more processors, causing the apparatus to function as:
   a first acquisition unit configured to, with a viewpoint set to a position of an object, acquire a plurality of environment maps for each position of light sources, the environment maps being obtained by imaging a surrounding environment from the viewpoint;
   a second acquisition unit configured to acquire a plurality of captured images for each position of the light sources, the captured images being obtained by imaging from a plurality of directions the object irradiated with light by the light sources;
   a segmentation unit configured to segment each of the plurality of environment maps into a plurality of solid angles by performing region segmentation based on a Voronoi diagram with points,
   wherein luminance in the environment map is larger than a predetermined value, set as kernel points; and
   a determination unit configured to determine reflection characteristics of the object based on the luminance corresponding to each of the plurality of solid angles and the plurality of captured images.

2. The apparatus according to claim 1, wherein, for each position of the light sources, the first acquisition unit acquires a plurality of the environment maps obtained by imaging a surrounding environment from the viewpoint by using an omnidirectional camera.

3. The apparatus according to claim 1, wherein, for each position of the light sources, the first acquisition unit acquires a plurality of the environment maps obtained by imaging a surrounding environment from the viewpoint by using a camera with a fish-eye lens.

4. The apparatus according to claim 1, wherein the first acquisition unit acquires the environment maps obtained by imaging an omnidirection from the viewpoint.

5. The apparatus according to claim 1, wherein, based on a luminance on the environment maps, the segmentation unit segments each of the plurality of environment maps into a plurality of solid angles.

6. The apparatus according to claim 5, wherein the segmentation unit segments the environment maps into a plurality of solid angles through a region segmentation using a Voronoi diagram with a kernel point set to a point where the luminance on the environment maps is larger than a predetermined value.

7. The apparatus according to claim 1, wherein, based on a predetermined allocation method, the segmentation unit segments each of the plurality of environment maps into a plurality of solid angles.

8. The apparatus according to claim 7, wherein the predetermined allocation method is determined based on an arrangement of the light sources.

9. The apparatus according to claim 1, wherein, for each of the plurality of solid angles, the determination unit determines the lighting direction based on an area center in the solid angles.

10. The apparatus according to claim 1, wherein, for each of the plurality of solid angles, the determination unit determines the lighting direction based on a luminance gravity center in the solid angles.

11. The apparatus according to claim 1, wherein the one or more memories storing instructions, when executed by the one or more processors, causes the apparatus to further function as:
    a third acquisition unit configured to acquire shape information about the object; and
    a generation unit configured to generate a shadowing map indicating whether incident light to the object is to be shadowed, based on the acquired shape information,
    wherein the determination unit determines the reflection characteristics of the object by applying the shadowing map to the environment maps.

12. The apparatus according to claim 11, wherein the shadowing map includes information indicating self-shading or self-shadowing at a point on the object.

13. The apparatus according to claim 11, wherein, in a case where information about reflection characteristics of the object lacks due to shadowing, the determination unit complements a portion of concern with similar reflection characteristics at a peripheral portion.

14. The apparatus according to claim 11,
    wherein the shadowing map includes information indicating a visible region, and
    wherein, based on the information indicating the visible region in the shadowing map, the determination unit generates a virtual environment map and a virtual line-of-sight map at a virtual position.

15. The apparatus according to claim 14, wherein, based on the information indicating the visible region, the determination unit segments the environment maps into segmentation solid angles and determines reflection characteristics of the object.

16. The apparatus according to claim 1, wherein the first acquisition unit acquires the plurality of environment maps with viewpoints set to a plurality of positions on the object.

17. The apparatus according to claim 1, wherein, at a point set on the object, the determination unit defines a coordinate system based on a normal vector, and describes the reflection characteristics based on the coordinate system.

18. A method comprising:
    acquiring, with a viewpoint set to a position of an object, a plurality of environment maps for each position of light sources, the environment maps being obtained by imaging a surrounding environment from the viewpoint;
    acquiring a plurality of captured images for each position of the light sources, the captured images being obtained by imaging from a plurality of directions the object irradiated with light by the light sources;
    segmenting each of the plurality of environment maps into a plurality of solid angles by performing region segmentation based on a Voronoi diagram with points, wherein luminance in the environment map is larger than a predetermined value, set as kernel points; and determining reflection characteristics of the object based on the luminance corresponding to each of the plurality of solid angles and the plurality of captured images.

19. A non-transitory computer-readable storage medium storing instructions that, when executed by a computer, cause the computer to perform a method comprising:

acquiring, with a viewpoint set to a position of an object, a plurality of environment maps for each position of light sources, the environment maps being obtained by imaging a surrounding environment from the viewpoint;

acquiring a plurality of captured images for each position of the light sources, the captured images being obtained by imaging from a plurality of directions the object irradiated with light by the light sources;

segmenting each of the plurality of environment maps into a plurality of solid angles by performing region segmentation based on a Voronoi diagram with points, wherein luminance in the environment map is larger than a predetermined value, set as kernel points; and determining reflection characteristics of the object based on the luminance corresponding to each of the plurality of solid angles and the plurality of captured images.

20. The apparatus according to claim 1, wherein the segmentation unit segments each of the plurality of environment maps into a plurality of solid angles such that a point having a luminance greater than a predetermined value is included in each solid angle.

\* \* \* \* \*